United States Patent
Zhou et al.

(10) Patent No.: US 10,603,206 B2
(45) Date of Patent: Mar. 31, 2020

(54) LATERAL PHARYNGEAL WALL TRACTOR AND IMPLANTATION METHOD

(71) Applicants: Xing Zhou, Guangzhou (CN); Xiangmin Zhang, Guangzhou (CN)

(72) Inventors: Xing Zhou, Guangzhou (CN); Xiangmin Zhang, Guangzhou (CN)

(*) Notice: Subject to any disclaimer, the term of this patent is extended or adjusted under 35 U.S.C. 154(b) by 398 days.

(21) Appl. No.: 15/600,216

(22) Filed: May 19, 2017

(65) Prior Publication Data

US 2017/0252204 A1     Sep. 7, 2017

Related U.S. Application Data

(63) Continuation of application No. PCT/CN2015/096892, filed on Dec. 10, 2015.

(30) Foreign Application Priority Data

Dec. 19, 2014 (CN) .......................... 2014 1 0805411

(51) Int. Cl.
*A61F 5/56* (2006.01)
*A61B 17/04* (2006.01)
(Continued)

(52) U.S. Cl.
CPC .......... *A61F 5/566* (2013.01); *A61B 17/0401* (2013.01); *A61B 17/24* (2013.01);
(Continued)

(58) Field of Classification Search
CPC ...... A61F 5/566; A61F 5/56; A61F 2005/563; A61F 2/20; A61F 2/00; A61F 5/08; A61C 7/08
See application file for complete search history.

(56) References Cited

U.S. PATENT DOCUMENTS

| 2005/0284485 A9 | 12/2005 | Nelson et al. |
| 2008/0035160 A1 | 2/2008 | Woodson et al. |

(Continued)

FOREIGN PATENT DOCUMENTS

| CN | 2619601 Y | 6/2004 |
| CN | 103961201 A | 8/2014 |
| CN | 204501174 U | 7/2015 |

(Continued)

OTHER PUBLICATIONS

Zhou, International Search Report and Written Opinion, PCT/CN2015/096892, dated Jan. 25, 2016, 20 pgs.
Zhou, International Preliminary Report on Patentability, PCT/CN2015/096892, dated Jun. 20, 2017, 6 pg.
(Continued)

*Primary Examiner* — Ophelia A Hawthorne
(74) *Attorney, Agent, or Firm* — Morgan, Lewis & Bockius LLP

(57) ABSTRACT

A lateral pharyngeal wall tractor including a bone fixer, a traction mechanism and a lateral pharyngeal wall fixer; wherein the lateral pharyngeal wall fixer is configured to be fixed on an M. palatopharyngeus or other submucous tissues of a lateral pharyngeal wall; the bone fixer is configured to be fixed on a processus alveolaris or a hamulus pterygoideus or a processus pterygoideus as a supporting point; one end of the traction mechanism is connected to the bone fixer, the other end is connected to the lateral pharyngeal wall fixer; the elastic traction force produced by the traction mechanism is greater than the collapse force of the lateral pharyngeal wall which is produced by negative pressure during inspiration, but is less than the contraction force which is produced by the muscle of the lateral pharyngeal wall during deglutition.

19 Claims, 18 Drawing Sheets

(51) Int. Cl.
    *A61B 17/24*     (2006.01)
    *A61F 2/20*     (2006.01)
    *A61B 17/02*     (2006.01)

(52) U.S. Cl.
    CPC .................. *A61F 2/20* (2013.01); *A61F 5/56* (2013.01); *A61B 17/02* (2013.01); *A61B 2017/044* (2013.01); *A61B 2017/0417* (2013.01); *A61B 2017/0448* (2013.01); *A61B 2017/0464* (2013.01); *A61B 2017/0496* (2013.01); *A61B 2017/248* (2013.01)

(56) References Cited

U.S. PATENT DOCUMENTS

| | | |
|---|---|---|
| 2008/0208265 A1 | 8/2008 | Frazier et al. |
| 2013/0085546 A1 | 4/2013 | Bolea et al. |
| 2013/0199542 A1 | 8/2013 | Summer |

FOREIGN PATENT DOCUMENTS

| | | |
|---|---|---|
| JP | 2006-507038 A | 3/2006 |
| JP | 2008-529608 T | 8/2008 |
| JP | 2013-544541 A | 12/2013 |
| WO | WO2014-117631 A1 | 8/2014 |

OTHER PUBLICATIONS

Preliminary Examination, MYPI2017702203, dated Oct. 20, 2017, 2 pgs.
Zhou, Examiner's Report, CA2971233, dated Jun. 6, 2018, 4 pgs.
Zhou, Notice of Reasons for Rejection, JP2017-532156, dated Aug. 28, 2018, 9 pgs.
Zhou, Decision to Grant, JP2017-532156, dated Apr. 22, 2019, 6 pgs.
Zhou, Notice to File Response, KR2017-7020074, dated Apr. 30, 2019, 5 pgs.
Office Action, CN201410805411.8, dated May 19, 2017, 3 pgs.
Zhou, Extended European Search Report, EP15869254.1, dated Aug. 13, 2018, 9 pgs.
Zhou, Communication Pursuant to Rules 70(2) and 70a(2), EP15869254.1, dated Aug. 30, 2018, 1 pg.

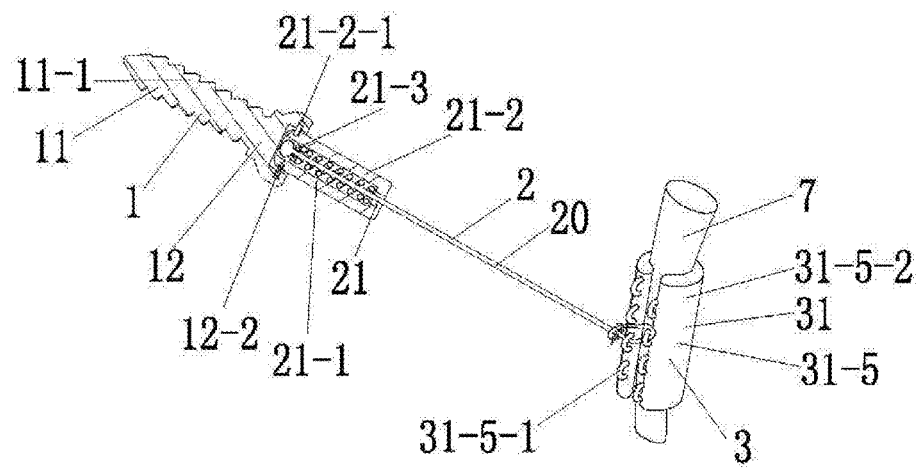
FIG. 10
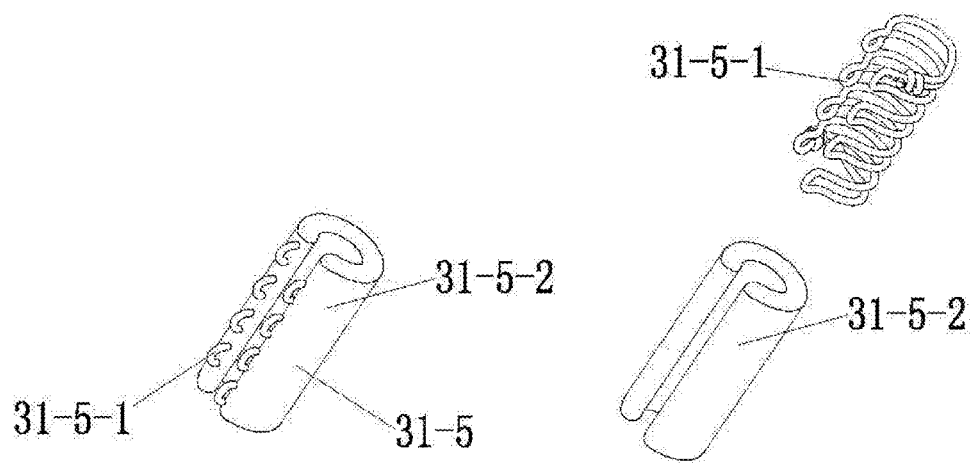
FIG. 10-1         FIG.10-2

LATERAL PHARYNGEAL WALL TRACTOR AND IMPLANTATION METHOD

PRIORITY CLAIM AND RELATED APPLICATIONS

This application is a continuation application of PCT Patent Application No. PCT/CN2015/096892, entitled "LATERAL WALL OF PHARYNX TRACTION DEVICE AND IMPLANTATION METHOD THEREFOR" filed on Dec. 10, 2015, which claims priority to Chinese Patent Application No. 201410805411.8, entitled "LATERAL PHARYNGEAL WALL TRACTOR AND IMPLANTATION METHOD" filed on Dec. 19, 2014, both of which are incorporated by reference in their entirety.

TECHNICAL FIELD

The present application relates to a tractor for being implanted in the oral cavity of a human body to outwardly pull a submucous tissue of a lateral pharyngeal wall and an implantation method, and in particular to a lateral pharyngeal wall tractor for treating the adult obstructive sleep apnea/hypopnea syndrome (hereinafter referred to as OSA) and an implantation method.

BACKGROUND

The adult obstructive sleep apnea/hypopnea syndrome is a sleep-disordered breathing disease with snoring and apnea as clinical characteristics which are caused by the collapse-caused obstruction of the upper airway during sleep. The main harm of OSA is the frequent occurrence of sleep apnea and hypopnea, which leads to the long-term decrease of blood oxygen saturation during sleep, thus causing a series of pathological changes of the human body, so the OSA has become a source disease of a variety of systemic diseases (diabetes, high blood pressure, coronary heart disease, cerebrovascular accident, etc.). According to statistics, the prevalence of OSA is up to 2% to 4% of the population at present, the incidence of OSA among middle-aged people is extremely high, and health and life quality are severely affected. Therefore, the international health organization has classified OSA as a major disease harming the health and life quality of the human being.

As for the pathogenesis of OSA, it's generally believed that the main cause is the collapse-caused obstruction of soft tissues due to the relaxation of the pharyngeal muscles maintaining the patency of the upper airway during sleep, and the obstructed plane includes the nasal part, the palatopharyngeal part and the glossopharyngeal part. Methods for treating OSA are carried out around relieving or exploiting these obstructed parts.

For the obstruction of the nasal part, a good surgical treatment effect can be achieved by nasal endoscopic surgery.

For the obstruction of the palatopharyngeal part caused by soft palate retropulsion, palatopharyngoplasty can be adopted. Uvulopalatopharyngoplasty has made a great contribution to the improvement of OSA patients' symptoms and after recover. Although surgical treatment means benefit innumerable patients, from the aspect of long-term effects, the excessive resection of mucous membrane and soft palate tissue structures will injure functional muscles, causing complications, such as nasal regurgitation during deglutition, open rhinolalia and nasopharyngeal stenosis and atresia.

For the obstruction of the glossopharyngeal part caused by tongue retropulsion, surgical methods, such as tongue volume reduction surgery, tongue advancement surgery, electrical tongue muscle stimulation surgery and tongue root traction, can be adopted for treatment. These surgical methods have respective advantages and disadvantages, and have certain treatment effects in relieving the obstruction of the glossopharyngeal part caused by tongue retropulsion.

In the pathogenesis of OSA, besides obstruction caused by soft palate retropulsion or tongue root retropulsion, negative pressure produced by inspiration during breathing can cause the collapse of the lateral pharyngeal wall, forming obstruction. Such obstruction caused by the collapse of the lateral pharyngeal wall has drawn more and more attention. Existing treatment methods are various lateral pharyngeal wall plasties, which mainly outwardly draw the muscles of the lateral pharyngeal wall, such as the M. palatopharyngeus, by surgical methods to achieve the purpose of enlarging the transverse diameter of the pharyngeal cavity to prevent airway obstruction. However, in the prior art, effective implantable medical instruments which can treat OSA caused by the collapse-caused obstruction of the lateral pharyngeal wall do not exist yet. Therefore, a novel implantable instrument needs to be provided to treat OSA caused by the collapse-caused obstruction of the lateral pharyngeal wall.

SUMMARY

The core of the present application is as follows: an implantable medical instrument—a lateral pharyngeal wall tractor (9)—is designed, a bone fixer (1) of the lateral pharyngeal wall tractor (9), which takes a processus alveolaris (81), a hamulus pterygoideus (82) or a processus pterygoideus (83) as a force-bearing supporting point, fixes a lateral pharyngeal wall fixer (3) on an M. palatopharyngeus (7) or other submucous tissues of a lateral pharyngeal wall, an elastic traction mechanism (2) is adopted for traction, one end of the traction mechanism (2) is connected to the bone fixer (1), the other end is connected to the lateral pharyngeal wall fixer (3), and as a result, the submucous tissue of the lateral pharyngeal wall, such as the M. palatopharyngeus (7), is outwardly drawn. The elastic traction force produced by the traction mechanism (2) is greater than the collapse force of the lateral pharyngeal wall which is produced by negative pressure during inspiration, but is less than the contraction force which is produced by the muscle of the lateral pharyngeal wall during deglutition. Thus, obstruction which is caused by the collapse of the lateral pharyngeal wall as the result of negative pressure produced by inspiration can be prevented, achieving the purpose of treating OSA; and meanwhile, affection on the deglutition function can be decreased as much as possible, keeping the deglutition function well. The specific technical solution is as follows:

The lateral pharyngeal wall tractor is characterized in that:

A, the lateral pharyngeal wall tractor (9) comprises a bone fixer (1), a traction mechanism (2) and a lateral pharyngeal wall fixer (3);

B, the bone fixer (1) is provided with a bone fixing mechanism (11) capable of being fixed on the processus alveolaris (81), the hamulus pterygoideus (82) or the processus pterygoideus (83) and a thread fixing mechanism (12) capable of fixing a traction thread; and the bone fixing mechanism (11) and the thread fixing mechanism (12) are connected together;

C, the traction mechanism (2) is a thread, a linear mechanism or a flat mechanism which is made of a material capable of being implanted in the human body for a long time; and D, the lateral pharyngeal wall fixer (3) comprises a lateral pharyngeal wall fixing mechanism (31) capable of being fixed on the lateral pharyngeal wall and a connecting mechanism (32) capable of being connected to the traction mechanism (2), and the lateral pharyngeal wall fixing mechanism (31) and the connecting mechanism (32) are connected together; and E, the bone fixing mechanism (11) of the bone fixer (1) is fixed on the processus alveolaris (81), hamulus pterygoideus (82) or processus pterygoideus (83) of the third molar of the maxilla; the lateral pharyngeal wall fixing mechanism (31) of the lateral pharyngeal wall fixer (3) is fixed on the M. palatopharyngeus (7) or other submucous tissues of the lateral pharyngeal wall; one end of the traction mechanism (2) is fixed on the connecting mechanism (32) of the lateral pharyngeal wall fixer (3), and the other end is fixed on the connecting mechanism (12) of the bone fixer (1); and the bone fixer (1) and the lateral pharyngeal wall fixer (3) are connected together through the traction mechanism (2).

Further, the bone fixing mechanism (11) of the bone fixer (1) comprises a bone nail (11-1).

The bone nail (11-1) is a threaded bone nail which is made of a material capable of being implanted in the human body for a long time. The threaded design can better ensure that the bone nail (11-1) cannot easily get loose when implanted into a bone structure, such as the processus alveolaris (81), consequently, installation is steadier, and it's safer in the process of long-term use.

The bone fixing mechanism (11) of the bone fixer (1) comprises a bone claw (11-2) which can be fixed on the hamulus pterygoideus (82) or the processus pterygoideus (83), and the bone claw (11-2) is provided with grip hooks (11-2-1). Since the design of the bone claw (11-2) is adopted, the installation process is convenient, that is, the lateral pharyngeal wall tractor only needs to clip a laminamedialis (83-1) or a laminalateralis (83-2) of the processus pterygoideus (83).

The bone fixing mechanism (11) of the bone fixer (1) comprises a connecting ring (11-3) which can be put on the hamulus pterygoideus (82), and the connecting ring (11-3) is provided with a through hole (11-3-1) through which the hamulus pterygoideus (82) can pass. Since the design of the connecting ring (11-3) is adopted, during installation, the connecting ring (11-3) only needs to be hung on the hamulus pterygoideus (82) through the through hole (11-3-1).

The bone fixing mechanism (11) of the bone fixer (1) comprises a support (11-4) which can be embedded in the processus pterygoideus (83), the support (11-4) is provided with supporting legs (11-4-1), and the supporting legs (11-4-1) are respectively fixed on the laminamedialis (83-1) and the laminalateralis (83-2) of the processus pterygoideus (83).

The bone fixing mechanism (11) of the bone fixer (1) comprises a connecting hook (11-5) which can be hung on the hamulus pterygoideus (82) or the processus pterygoideus (83).

Further, the traction mechanism (2) comprises a thread (20) which is made of a material capable of being implanted in the human body for a long time.

The thread (20) is a thread with elasticity.

The traction mechanism (2) comprises an elasticity generator (21) which can generate elastic traction force.

The elasticity generator (21) comprises a spring mechanism (21-1). The spring mechanism (21-1) of the elasticity generator (21) can has a variety of different specific designs, which will not be introduced herein one by one.

The elasticity generator (21) comprises the spring mechanism (21-1), a shell (21-2) and a slider (21-3) capable of being connected to the thread (20); and the spring mechanism (21-1) and the slider (21-3) are movably installed in the shell (21-2).

The traction mechanism (2) comprises at least one elasticity generator (21); the elasticity generators (21) are arranged at both ends of the traction mechanism (2), or the elasticity generator (21) is arranged in the middle of the traction mechanism (2).

The elastic traction force produced by the traction mechanism (2) is greater than the collapse force of the lateral pharyngeal wall which is produced by negative pressure during inspiration, but is less than the contraction force which is produced by the muscle of the lateral pharyngeal wall during deglutition. Normally, the elastic traction force of the traction mechanism (2) is greater than 10 gf and less than 300 gf. The preferred value of the elastic traction force of the traction mechanism (2) is between 10 gf and 80 gf.

Further, the lateral pharyngeal wall fixing mechanism (31) of the lateral pharyngeal wall fixer (3) is a binding thread (31-1), a binding strap (31-2), a fixing hook (31-3), a tissue clip (31-4) or a curved fixing plate (31-5) which can be tied or fixed on the submucous tissue of the lateral pharyngeal wall.

The curved plate (31-5) is a C-shaped or U-shaped curved plate. Of course, the curved plate (31-5) can also be designed into curved plates with other shapes, such as a conical curved plate with an opening, and without departing from the protection scope of the present application, those skilled in the art also can design other effective curved plates, which will not be introduced herein one by one.

The curved plate (31-5) is a curved plate with a combined structure, the curved plate (31-5) with the combined structure comprises a reinforcing rib (31-5-1) and a film (31-5-2), and the film (31-5-2) is attached to the reinforcing rib (31-5-1).

The reinforcing rib (31-5-1) or the film (31-5-2) can be elastically deformed under the action of external force, and can be restored or nearly restored to the original shape after the external force is removed.

The curved fixing plate (31-5) adopts a single wire-wound helical C-shaped curved plate. Specially, a titanium-nickel shape-memory alloy wire can be adopted to produce the curved fixing plate (31-5). Other medical elastic materials can also be adopted for production.

The lateral pharyngeal wall tractor (9) comprises a bone fixer (1), a traction mechanism (2) and a lateral pharyngeal wall fixer (3). The lateral pharyngeal wall fixer (3) is fixed on the M. palatopharyngeus (7) or other submucous tissues of the lateral pharyngeal wall. With the bone fixer (1) fixed on the processus alveolaris (81), the hamulus pterygoideus (82) or the processus pterygoideus (83) as a supporting point, one end of the traction mechanism (2) is connected to the bone fixer (1), the other end is connected to the lateral pharyngeal wall fixer (3), and as a result, the submucous tissue of the lateral pharyngeal wall is pulled outward. The elastic traction force produced by the traction mechanism (2) is greater than the collapse force of the lateral pharyngeal wall which is produced by negative pressure during inspiration, but is less than the contraction force which is produced by the muscle of the lateral pharyngeal wall during deglutition. Thus, obstruction which is caused by the collapse of the lateral pharyngeal wall as the result of negative pressure produced by inspiration can be presented, achieving the purpose of treating OSA; and meanwhile, affection on the deglutition function can be decreased as much as possible, keeping the deglutition function well.

Implantation Method of the Present Invention

According to the different structures of specific products, an implantation method of the lateral pharyngeal wall tractor (9) of the present application can be divided into five types: an implantation method for a bone nail type lateral pharyngeal wall tractor, an implantation method for a bone claw type lateral pharyngeal wall tractor, an implantation method for a connecting ring type lateral pharyngeal wall tractor, an implantation method for a support type lateral pharyngeal wall tractor and an implantation method for a connecting hook type lateral pharyngeal wall tractor.

Implantation method 1: the implantation method for the bone nail type lateral pharyngeal wall tractor of the present application:

Step 1: Under local anaethesia or general anaethesia, a mouth gag is put in, a vertical mucosal incision is made in the surface of a hamulus pterygoideus (82), an upper processus alveolaris (81) and the hamulus pterygoideus (82) are separated and exposed, a right-angled drill is used to drill a bone hole (81-1) matched with a bone nail (11-1) in the upper processus alveolaris (81) of the third molar, and the bone nail (11-1) is fitted in and fixed. If the bone nail (11-1) is a self-tapping screw type bone nail, the bone nail (11-1) can be directly fixed in the upper processus alveolaris (81) without needing to use the right-angled drill to make the bone hole (81-1) in the upper processus alveolaris (81) of the third molar.

Step 2: An arc-shaped incision which is about 15 mm long is made along the upper end of a palatoglossal arch, an M. palatopharyngeus (7) is separated and exposed, or after routine UPPP, the M. palatopharyngeus (7) is exposed.

Step 3: A special tool is used to put in the lateral pharyngeal wall tractor (9) along the vertical mucosal incision of the surface of the hamulus pterygoideus (82), a lateral pharyngeal wall fixing mechanism (31) of a lateral pharyngeal wall fixer (3) is fixed on a submucous tissue of a lateral pharyngeal wall, such as the M. palatopharyngeus (7), by a method of claim 15, and then after being connected to a connecting mechanism (12) of a bone fixer (1), a traction mechanism (2) is connected to the bone nail (11-1) of a bone fixing mechanism (11).

Step 4: The tightness of the traction mechanism (2) is adjusted, the incision is sutured, and a surgery is performed on the opposite side in the same way.

Implantation method 2: the implantation method for the bone claw type lateral pharyngeal wall tractor of the present application:

Step 1: Under local anaethesia or general anaethesia, a mouth gag is put in, a vertical mucosal incision is made in the surface of a hamulus pterygoideus (82), the hamulus pterygoideus (82) or a processus pterygoideus (83) is separated and exposed, and grip hooks (11-2-1) of a bone claw (11-2) of a bone fixing mechanism (11) of a bone fixer (1) grip the hamulus pterygoideus (82) or the processus pterygoideus (83).

Step 2: An arc-shaped incision which is about 15 mm long is made along the upper end of a palatoglossal arch, an M. palatopharyngeus (7) is separated and exposed, or after routine UPPP, the M. palatopharyngeus (7) is exposed.

Step 3: A special tool is used to put in the lateral pharyngeal wall tractor (9) along the vertical mucosal incision of the surface of the hamulus pterygoideus, a lateral pharyngeal wall fixing mechanism (31) of a lateral pharyngeal wall fixer (3) is fixed on a submucous tissue of a lateral pharyngeal wall, such as the M. palatopharyngeus (7), by a method of claim 15, and after being connected to a connecting mechanism (12) of a bone fixer (1), a traction mechanism (2) is connected to the bone claw (11-2) of the bone fixing mechanism (11).

Step 4: The tightness of the traction mechanism (2) is adjusted, the incision is sutured, and a surgery is performed on the opposite side in the same way.

Implantation method 3: the implantation method for the connecting ring type lateral pharyngeal wall tractor of the present application:

Step 1: Under local anaethesia or general anaethesia, a mouth gag is put in, a vertical mucosal incision is made in the surface of a hamulus pterygoideus (82), and the hamulus pterygoideus (82) is separated and exposed.

Step 2: An arc-shaped incision which is about 15 mm long is made along the upper end of a palatoglossal arch, an M. palatopharyngeus (7) is separated and exposed, or after routine UPPP, the M. palatopharyngeus (7) is exposed.

Step 3: A special tool is used to put in the lateral pharyngeal wall tractor (9) along the vertical mucosal incision of the surface of the hamulus pterygoideus, a lateral pharyngeal wall fixing mechanism (31) of a lateral pharyngeal wall fixer (3) is fixed on a submucous tissue of a lateral pharyngeal wall, such as the M. palatopharyngeus (7), by a method of claim 15, a traction mechanism (2) is connected to a connecting mechanism (12) of a bone fixer (1), and a connecting ring (11-3) of the bone fixer (1) is put on the hamulus pterygoideus (82).

Step 4: The tightness of the traction mechanism (2) is adjusted, the incision is sutured, and a surgery is performed on the opposite side in the same way.

Implantation method 4: the implantation method for the support type lateral pharyngeal wall tractor of the present application:

Step 1: Under local anaethesia or general anaethesia, a mouth gag is put in, a vertical mucosal incision is made in the surface of a hamulus pterygoideus (82), a processus pterygoideus (83) is separated and exposed, and two through holes are respectively made in a laminamedialis (83-1) and a laminalateralis (83-2) of the processus pterygoideus (83).

Step 2: An arc-shaped incision which is about 15 mm long is made along the upper end of a palatoglossal arch, an M. palatopharyngeus (7) is separated and exposed, or after routine UPPP, the M. palatopharyngeus (7) is exposed.

Step 3: A special tool is used to put in the lateral pharyngeal wall tractor (9) along the vertical mucosal incision of the surface of the hamulus pterygoideus (82), a lateral pharyngeal wall fixing mechanism (31) of a lateral pharyngeal wall fixer (3) is fixed on a submucous tissue of a lateral pharyngeal wall, such as the M. palatopharyngeus (7), by a method of claim 15, a traction mechanism (2) is connected to a connecting mechanism (12) of a bone fixer (1), and supporting legs (11-4-1) of a support (11-4) of the bone fixer (1) are respectively inserted into the through holes of the laminamedialis (83-1) and laminalateralis (83-2) of the processus pterygoideus (83).

Step 4: The tightness of the traction mechanism (2) is adjusted, the incision is sutured, and a surgery is performed on the opposite side in the same way.

Implantation method 5: the implantation method for the connecting hook type lateral pharyngeal wall tractor of the present application:

Step 1: Under local anaethesia or general anaethesia, a mouth gag is put in, a vertical mucosal incision is made in the surface of a hamulus pterygoideus (82), the hamulus pterygoideus (82) and a processus pterygoideus (83) are separated and exposed, and a through hole is made in a laminamedialis (83-1) or a laminalateralis (83-2) of the processus pterygoideus (83).

Step 2: An arc-shaped incision which is about 15 mm long is made along the upper end of a palatoglossal arch, an M. palatopharyngeus (7) is separated and exposed, or after routine UPPP, the M. palatopharyngeus (7) is exposed.

Step 3: A special tool is used to put in the lateral pharyngeal wall tractor (9) along the vertical mucosal incision of the surface of the hamulus pterygoideus (82), a lateral pharyngeal wall fixing mechanism (31) of a lateral pharyngeal wall fixer (3) is fixed on a submucous tissue of a lateral pharyngeal wall, such as the M. palatopharyngeus (7), by a method of claim 15, a traction mechanism (2) is connected to a connecting mechanism (12) of a bone fixer (1), and a connecting hook (11-5) of the bone fixer (1) is hung on the hamulus pterygoideus (82), or passes through and is fixed in the through hole of the laminamedialis (83-1) or laminalateralis (83-2) of the processus pterygoideus (83).

Step 4: The tightness of the traction mechanism (2) is adjusted, the incision is sutured, and a surgery is performed on the opposite side in the same way.

BRIEF DESCRIPTION OF THE DRAWINGS

FIG. 1-1 is a section view of FIG. 1.

FIG. 1-2 is an operating principle diagram of FIG. 1.

FIG. 2 is a structural schematic diagram of the bone nail type lateral pharyngeal wall tractor with an elasticity generator in the present application.

FIG. 2-1 is a stereostructural schematic diagram of FIG. 2.

FIG. 2-2 is a section view of FIG. 2.

FIG. 2-3 is an operating principle diagram of FIG. 2.

FIG. 3 is a structural schematic diagram of a support type lateral pharyngeal wall tractor in the present application.

FIG. 3-1 is a section view of FIG. 3.

FIG. 3-2 is an operating principle diagram of FIG. 3.

FIG. 4-1 is a section view of FIG. 4.

FIG. 4-2 is an operating principle diagram of FIG. 4.

FIG. 5-1 is a section view of FIG. 5.

FIG. 5-2 is an operating principle diagram of FIG. 5.

FIG. 6-1 is a section view of FIG. 6.

FIG. 6-2 is an operating principle diagram of FIG. 6.

FIG. 10 is a structural schematic diagram of a combined-structure curved plate type lateral pharyngeal wall tractor in the present application.

FIG. 10-1 is a structural schematic diagram of a combined-structure curved plate type lateral pharyngeal wall fixing mechanism in the present application.

FIG. 10-2 is an exploded view of FIG. 10-1.

FIG. 14-1 is a structural schematic diagram of an open tissue clip in FIG. 14.

FIG. 15-1 is a structural schematic diagram of an open tissue clip in FIG. 15.

Figure 1:
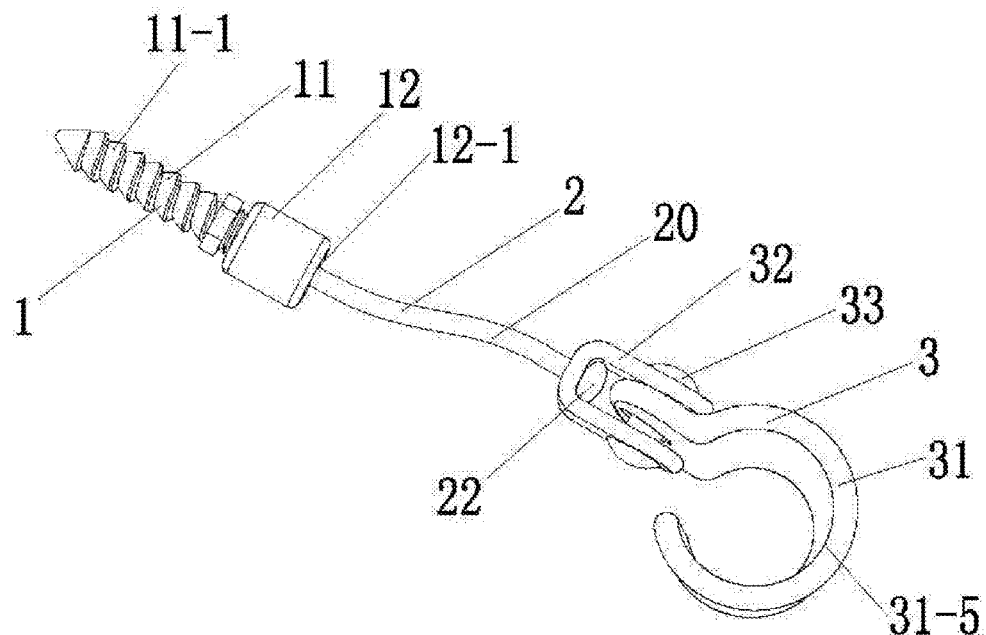
FIG. 1 is a structural schematic diagram of a bone nail type lateral pharyngeal wall tractor in the present application.
Figure 1:
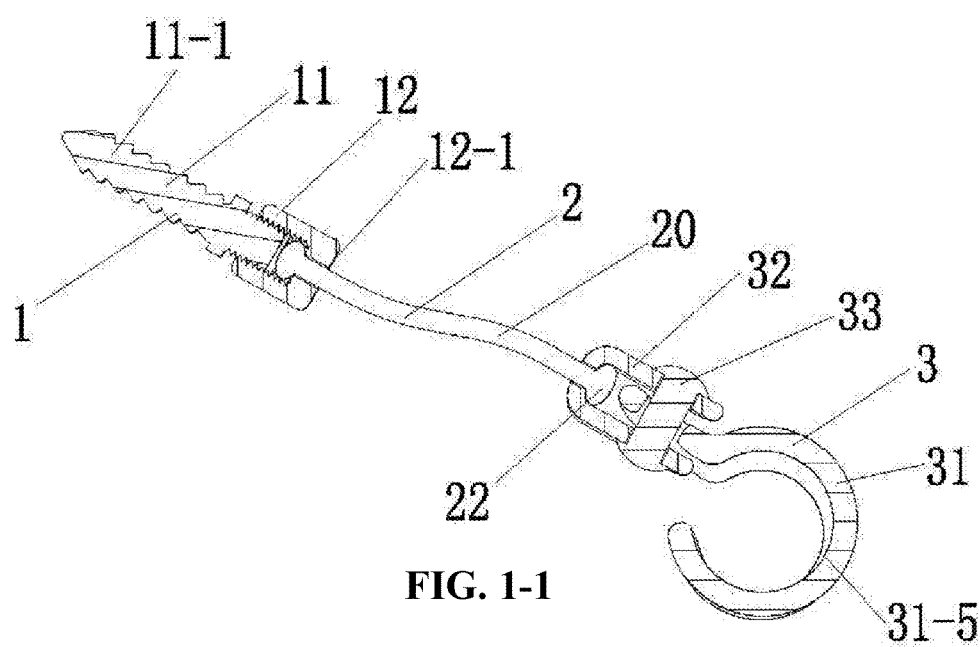

The meanings of the serial numbers in the above drawings are as follows:

1 is a bone fixer, 2 is a traction mechanism, and 3 is a lateral pharyngeal wall fixer; 7 is an M. palatopharyngeus; 81 is a processus alveolaris, 81-1 is a bone hole made in the processus alveolaris, 82 is a hamulus pterygoideus, 83 is a processus pterygoideus, 83-1 is a laminamedialis of the processus pterygoideus, 83-2 is a laminalateralis of the processus pterygoideus, 83-1-1 is a through hole in the laminamedialis, and 83-2-1 is a through hole in the laminalateralis; and 9 is the lateral pharyngeal wall tractor of the present application.

11 is a bone fixing mechanism, and 12 is a connecting mechanism for connection with the traction mechanism on the bone fixer.

11-1 is a bone nail, 11-2 is a bone claw, 11-3 is a connecting ring, 11-4 is a support, and 11-5 is a connecting hook; 12-1 is a through hole of the end of the connecting mechanism of the bone fixer, 12-2 is a positioning plate of the connecting mechanism, and 12-3 is a connecting hook on the connecting mechanism at the tail of the bone claw;

11-1-1 is a threaded structure on the bone nail; 11-2-1 is grip hooks on the bone claw; 11-3-1 is a through hole on the connecting ring; and 11-4-1 is supporting legs on the support.

20 is a thread; 21 is an elasticity generator, 21-1 is a spring mechanism, 21-2 is a shell, and 21-3 is a slider; 22 is connecting bosses, and 23 is a through hole.

21-2-1 is a positioning groove in the shell; and 21-3-1 is a connecting hook of the slider.

31 is a lateral pharyngeal wall fixing mechanism; 31-1 is a binding thread, 31-2 is a binding strap, 31-3 is a fixing hook, 31-4 is a tissue clip, and 31-5 is a curved fixing plate; 32 is a connecting mechanism of the lateral pharyngeal wall fixer, and 32-1 is a through hole of the bottom of the connecting mechanism of the lateral pharyngeal wall fixer.

31-4-1 is a left arm of the tissue clip, 31-4-2 is a right arm of the tissue clip, 31-4-3 is occludable teeth on the left arm and the right arm, 31-4-4 is a through hole for connection with the maxilla traction mechanism in the tissue clip, and 31-4-5 is handles of the tissue clip; 31-5-1 is a reinforcing rib on the curved fixing plate, and 31-5-2 is a film on the curved fixing plate.

DESCRIPTION OF EMBODIMENTS

Embodiment 1: A Bone Nail Type Lateral Pharyngeal Wall Tractor in the Present Application Referring to FIG. 1 and FIG. 1-2, the lateral pharyngeal wall tractor (9) in the present embodiment comprises a bone fixer (1), a traction mechanism (2) and a lateral pharyngeal wall fixer (3);

The bone fixer (1) is provided with a bone fixing mechanism (11) capable of being fixed on a processus alveolaris (81) and a thread connecting mechanism (12) capable of fixing a traction thread; and the bone fixing mechanism (11) and the connecting mechanism (12) are connected together. In the present embodiment, a detachable threaded connection method is adopted between the bone fixing mechanism (11) and the connecting mechanism (12).

In the present embodiment, the bone fixing mechanism (11) is a threaded bone nail (11-1) which is made of titanium alloy capable of being implanted in the human body for a long time. The threaded design can better ensure that the bone nail (11-1) cannot easily get loose when implanted into the processus alveolaris (81), consequently, installation is steadier, and it's safer in the process of long-term use. The end of the connecting mechanism (12) of the bone fixer (1) is provided with a through hole (12-1), and the size of the through hole (12-1) is matched with the size of the traction mechanism (2).

The traction mechanism (2) is a thread (20) with elasticity which can be implanted in the human body for a long time. Both ends of the thread (20) are provided with connecting bosses (22) which can be connected to the connecting mechanism (12) of the bone fixer (1) and a connecting mechanism (32) of the lateral pharyngeal wall fixer (3). The connecting bosses (22) can be formed by the method of tying the thread or riveting connectors at the ends of the thread. Only two production methods for the connecting bosses (22) are introduced herein, and without departing from the protection scope of the present application, those skilled in the art also can design other effective production methods, which are not introduced herein one by one.

The lateral pharyngeal wall fixer (3) comprises a lateral pharyngeal wall fixing mechanism (31) capable of being fixed on an M. palatopharyngeus (7) and the connecting mechanism (32) capable of fixing the traction mechanism (2), and the lateral pharyngeal wall fixing mechanism (31) and the connecting mechanism (32) are connected together.

The lateral pharyngeal wall fixing mechanism (31) of the lateral pharyngeal wall fixer (3) is a C-shaped curved plate (31-5) which can be fixed on the M. palatopharyngeus (7). The C-shaped curved plate can be conveniently mounted on the M. palatopharyngeus (7), and also has a large contact area with the M. palatopharyngeus (7), and the cutting of the M. palatopharyngeus can be avoided.

The bottom of the connecting mechanism (32) of the lateral pharyngeal wall fixer (3) is provided with a through hole (32-1), and the size of the through hole (32-1) is matched with the size of the thread (20) of the traction mechanism (2). The C-shaped curved plate (31-5) of the lateral pharyngeal wall fixing mechanism (31) and the connecting mechanism (32) are connected together through a pin (33).

During product assembly, the C-shaped curved plate (31-5) is connected to the connecting mechanism (32) through the pin (33), one end of the thread (20) then passes through the through hole (32-1) of the bottom of the connecting mechanism (32) of the lateral pharyngeal wall fixer (3), and is then tied or connected with one connector by riveting, so that one connecting boss (22) is formed. After passing through the through hole (12-1) of the end of the connecting mechanism (12) of the bone fixer (1), the other end of the thread (20) is tied or connected with the other connector by riveting, so that the other connecting boss (22) is formed. Finally, the bone fixing mechanism (11) of the bone fixer (1) and the thread connecting mechanism (12) are connected together by threads.

Figures 1, 2:
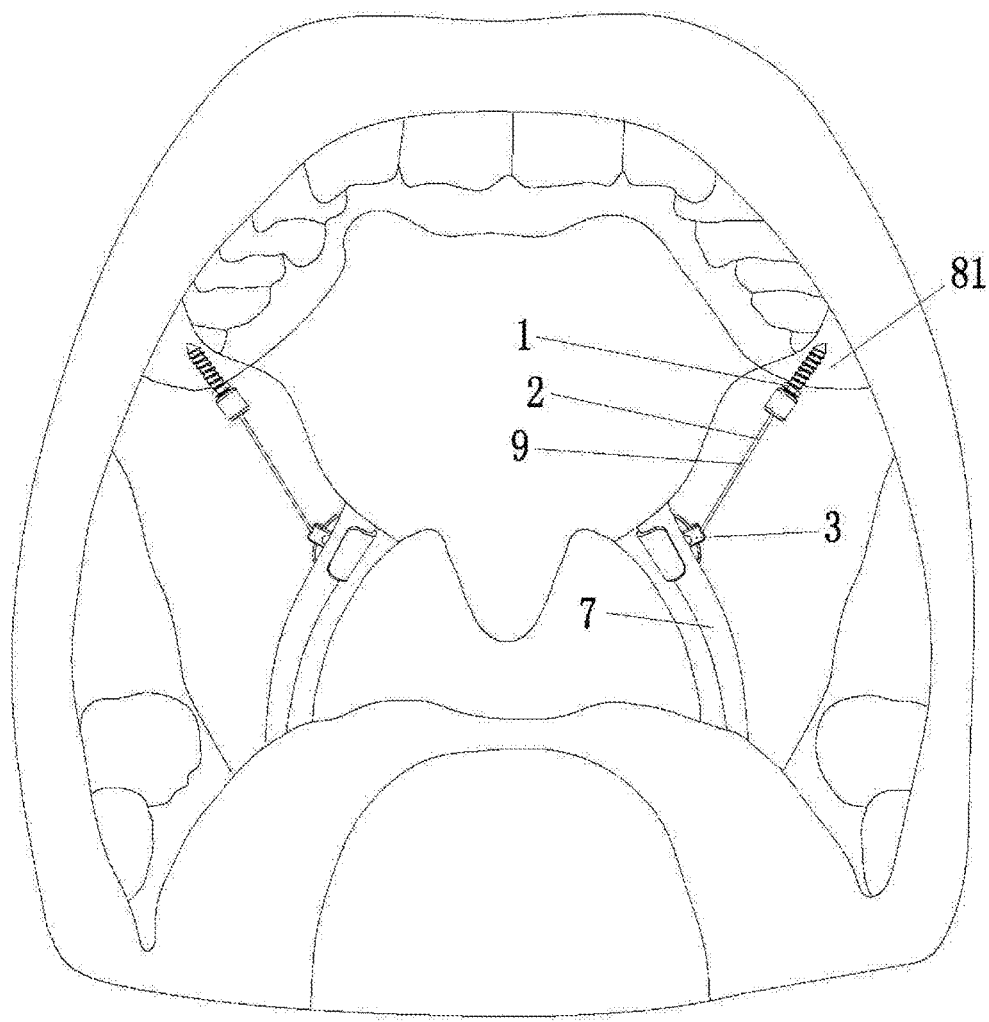

Referring to FIG. 1-2, the implantation method of the present embodiment is as follows:

Step 1: Under general anaesthesia, a mouth gag is put in, a vertical mucosal incision is made in the surface of a hamulus pterygoideus (82), an upper processus alveolaris (81) and the hamulus pterygoideus (82) are separated and exposed, a right-angled drill is used to drill a bone hole (81-1) matched with a bone nail (11-1) in the upper processus alveolaris (81) of the third molar, and the threaded bone nail (11-1) is screwed into the bone hole (81-1). If the bone nail (11-1) is a self-tapping screw design, the bone nail (11-1) can be directly installed in the upper processus alveolaris (81) without needing to use the right-angled drill to make the bone hole (81-1) in the upper processus alveolaris (81) of the third molar.

Step 2: An arc-shaped incision which is about 15 mm long is made along the upper end of a palatoglossal arch, and an M. palatopharyngeus (7) is separated and exposed.

Step 3: A lateral pharyngeal wall tractor (9) is put in along the vertical mucosal incision of the surface of the hamulus pterygoideus (82), a fixing hook (31-3) of a lateral pharyngeal wall fixing mechanism (31) of a lateral pharyngeal wall fixer (3) is fixed on the M. palatopharyngeus (7), and then after being connected to a connecting mechanism (12) of a bone fixer (1), a traction mechanism (2) is connected to the bone nail (11-1) of a bone fixing mechanism (11).

Step 4: The tightness of the traction mechanism (2) is adjusted, the incision is sutured, and a surgery is performed on the opposite side in the same way.

The elastic traction force of the traction mechanism (2) is greater than the collapse force of the lateral pharyngeal wall which is produced by negative pressure during inspiration, but is less than the contraction force of the muscle of the lateral pharyngeal wall during deglutition. Normally, the elastic traction force of the traction mechanism (2) is greater than 10 gf and less than 300 gf. The preferred value of the elastic traction force of the traction mechanism (2) is between 10 gf and 80 gf.

After the lateral pharyngeal wall tractor (9) of the present application is implanted into a patient, after negative pressure causes the collapse of the lateral pharyngeal wall during inspiration, since the traction mechanism (2) produces elastic traction force greater than collapse force, the elastic traction force produced by the traction mechanism (2) can outwardly draw the muscle of the lateral pharyngeal wall, such as the M. palatopharyngeus (7). Since the elastic traction force of the traction mechanism (2) is less than the contraction force of the muscle of the lateral pharyngeal wall at the same time during deglutition, when being worn, the lateral pharyngeal wall tractor (9) can decrease affection on the deglutition function as much as possible, keeping the deglutition function well. Implanting the lateral pharyngeal wall tractor (9) of the present application not only can prevent obstruction which is caused by the collapse of the lateral pharyngeal wall as the result of negative pressure produced by inspiration, achieving the purpose of treating OSA, but also can keep the deglutition function well.

Embodiment 2: A Bone Nail Type Lateral Pharyngeal Wall Tractor with an Elasticity Generator in the Present Application Referring to FIG. 2 to FIG. 3, the difference between the present embodiment and embodiment 1 is that in the present embodiment, a traction mechanism (2) comprises the elasticity generator (21) which can generate elastic traction force. Since the traction mechanism (2) is provided with the elasticity generator (21), when the traction mechanism (2) receives the action of great external force, the elasticity generator (21) can produce a cushioning effect, so that the traction mechanism (2) cannot correspondingly produce excessive traction force due to the action of the great external force to cause the discomfort of a patient and affect deglutition.

The elasticity generator (21) comprises a spring mechanism (21-1), a shell (21-2) and a slider (21-3). The spring mechanism (21-1) and the slider (21-3) are movably installed in the shell (21-2), and the traction mechanism (2) can be fixed on the slider (21-3). In the present embodiment, because the shell (21-2) of the elasticity generator (21) is arc-shaped, after being fixed in a processus alveolaris (81), a bone nail (11-1) can conveniently pass through the space between a laminamedialis (83-1) and a laminalateralis (83-2) of a processus pterygoideus (83) to guide a thread (20) of the traction mechanism (2) to a lateral pharyngeal wall, effectively preventing the bone tissues of the laminamedialis (83-1) and laminalateralis (83-2) of the processus pterygoideus (83) from cutting off the thread (20). As a tissue of the lateral pharyngeal wall, such as an M. palatopharyngeus (7), moves, a C-shaped curved plate (31-5) fixed on the M. palatopharyngeus (7) also moves along with the M. palatopharyngeus (7), causing the thread (20) to move. The motion of the thread (20) can cause the motion of the slider (21-3), and as a result, the spring mechanism (21-1) is compressed to produce moderate elastic traction force.

The elasticity generator (21) is mounted at the end of the traction mechanism (2) which is connected to a bone fixer (1), and the shell (21-2) is provided with a positioning groove (21-2-1). A connecting mechanism (12) of the bone fixer (1) is provided with a positioning plate (12-1). When the end of the shell (21-2) is inserted into the cavity of the connecting mechanism (12) of the bone fixer (1), the positioning plate (12-2) of the connecting mechanism (12) can be embedded in the positioning groove (21-2-1) of the shell (21-2), forming concave-convex engagement connection. Of course, without departing from the protection scope of the present application, those skilled in the art also can design other connection methods, such as threaded connection, concave-convex engagement connection and interference fit connection, which will not be introduced herein one by one.

Figure 2:
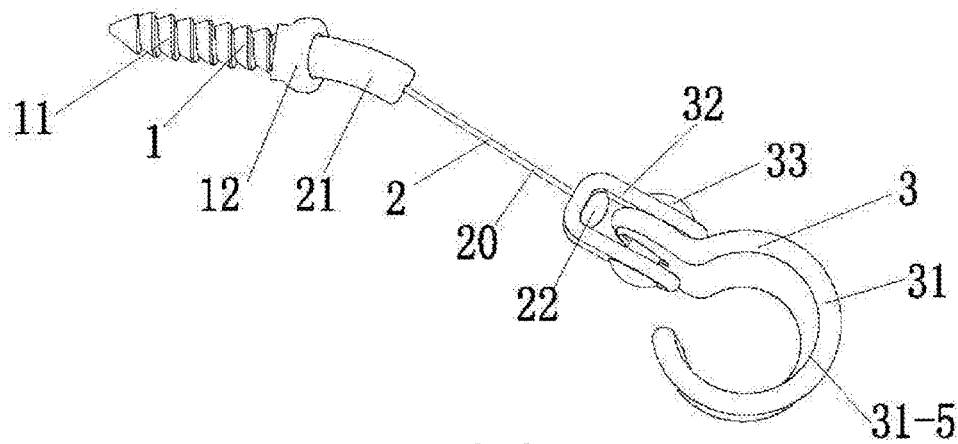
Figures 1, 2:
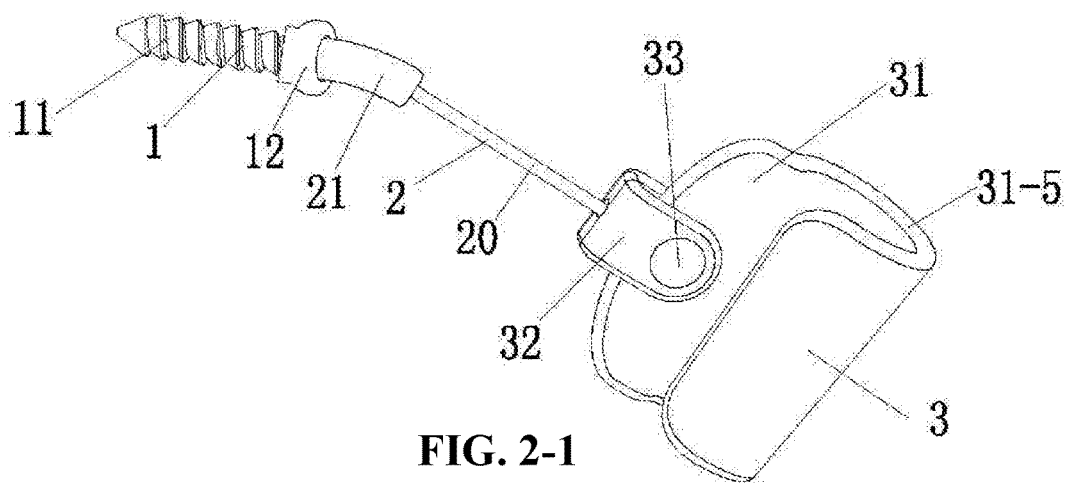
Figure 2:
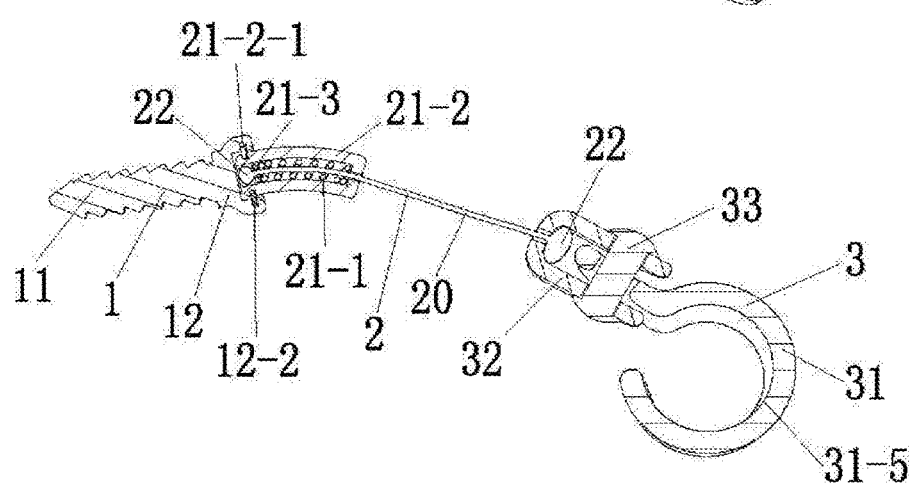
Figures 2, 3:
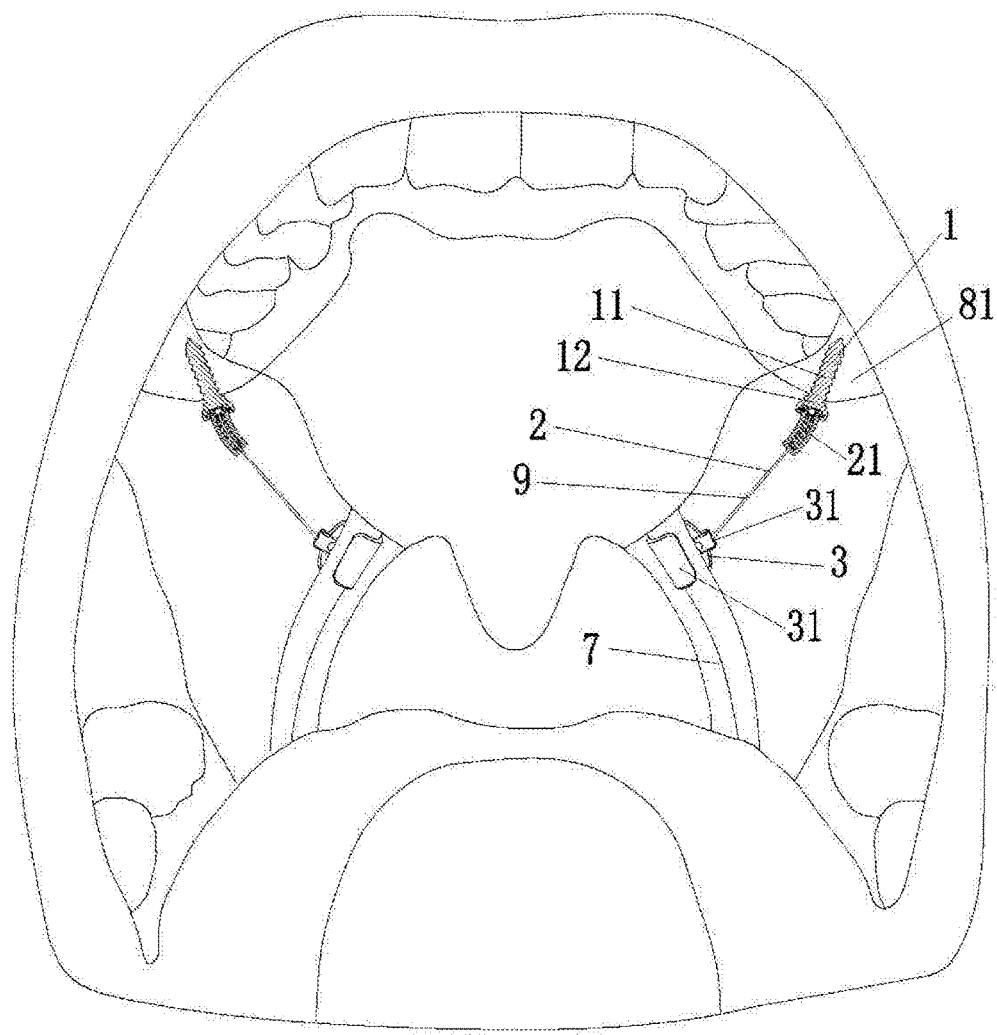
Figure 3:
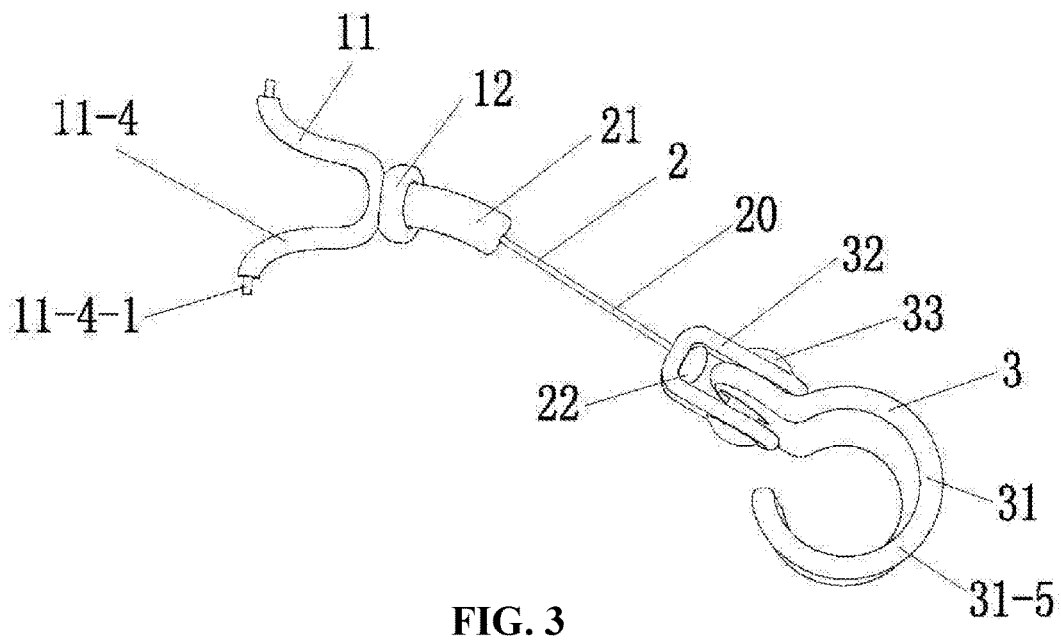
Figures 1, 3:
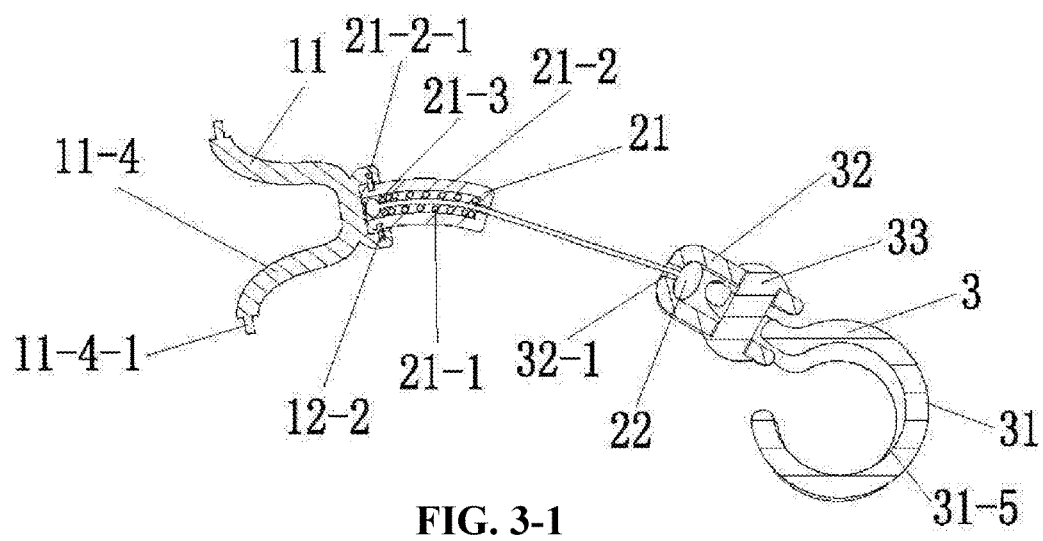
Figures 2, 3:
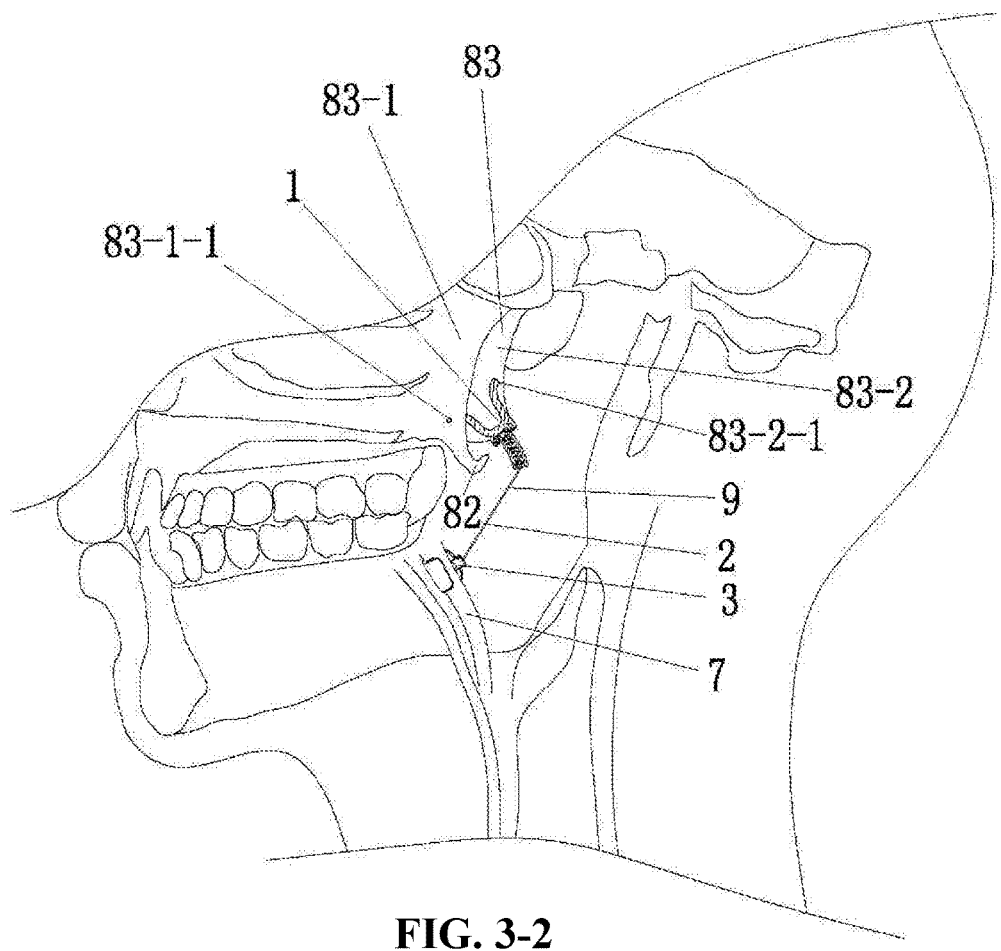

Referring to FIG. 2-3, after the lateral pharyngeal wall tractor of the present application is implanted, since the traction mechanism (2) is provided with the elasticity generator (21), by adjusting the spring mechanism (21-1) of the elasticity generator (21), the elastic traction force of the traction mechanism (2) can be perfectly set in an ideal range. While always keeping moderate traction force, the elasticity generator (21) can play a good force-cushioning role, and consequently, not only can the effect of outwardly drawing the tissue of the lateral pharyngeal wall be ensured, achieving the purpose of treating OSA, but also the comfort and the function of deglutition are ensured.

Embodiment 3: A Lateral Pharyngeal Wall Tractor with a Support Type Bone Fixer in the Present Application Referring to FIG. 3 and FIG. 3-2, the difference between the present embodiment and embodiment 2 is that in the present embodiment, a bone fixing mechanism (11) of the bone fixer (1) comprises a support (11-4). The support comprises two supporting legs (11-4-1), which are respectively arranged on the left and the right. The supporting legs (11-4-1) on the left and the right can be respectively embedded in a through hole (83-1-1) and a through hole (83-2-1) which are made in a laminamedialis (83-1) and a laminalateralis (83-2) of a processus pterygoideus (83), forming fixed supporting.

Referring to FIG. 3-2, in a clinical surgery:

Step 1: Under local anaethesia or general anaethesia, a mouth gag is put in, a vertical mucosal incision is made in the surface of a hamulus pterygoideus (82), a processus pterygoideus (83) is separated and exposed, and a through hole (83-1-1) and a through hole (83-2-1) are respectively made in a laminamedialis (83-1) and a laminalateralis (83-2) of a processus pterygoideus (83).

Step 2: An arc-shaped incision which is about 15 mm long is made along the upper end of a palatoglossal arch, and an M. palatopharyngeus (7) is separated and exposed.

Step 3: A special tool is used to put in the lateral pharyngeal wall tractor (9) along the vertical mucosal incision of the surface of the hamulus pterygoideus (82), a fixing hook (31-3) of a lateral pharyngeal wall fixing mechanism (31) of a lateral pharyngeal wall fixer (3) is fixed on the M. palatopharyngeus (7), a traction mechanism (2) is connected to a connecting mechanism (12) of the bone fixer (1), and the supporting legs (11-4-1) of the support (11-4) of the bone fixer (1) are respectively inserted into the through hole (83-1-1) and the through hole (83-2-1) made in the laminamedialis (83-1) and laminalateralis (83-2) of the processus pterygoideus (83).

Step 4: The tightness of the traction mechanism (2) is adjusted, the incision is sutured, and a surgery is performed on the opposite side in the same way.

Embodiment 4: A Lateral Pharyngeal Wall Tractor with a Connecting Hook Type Bone Fixer in the Present Application Referring to FIG. 4 and FIG. 4-2, the difference between the present embodiment and embodiment 2 is that in the present embodiment, a bone fixing mechanism (11) of the bone fixer (1) comprises a connecting hook (11-5). The connecting hook (11-5) can pass through a through hole (83-1-1) made in a laminamedialis (83-1) of a processus pterygoideus (83), and is fixedly connected to the laminamedialis. Or the connecting hook (11-5) is directly hung on a hamulus pterygoideus (82) to form fixed connection.

Figure 4:
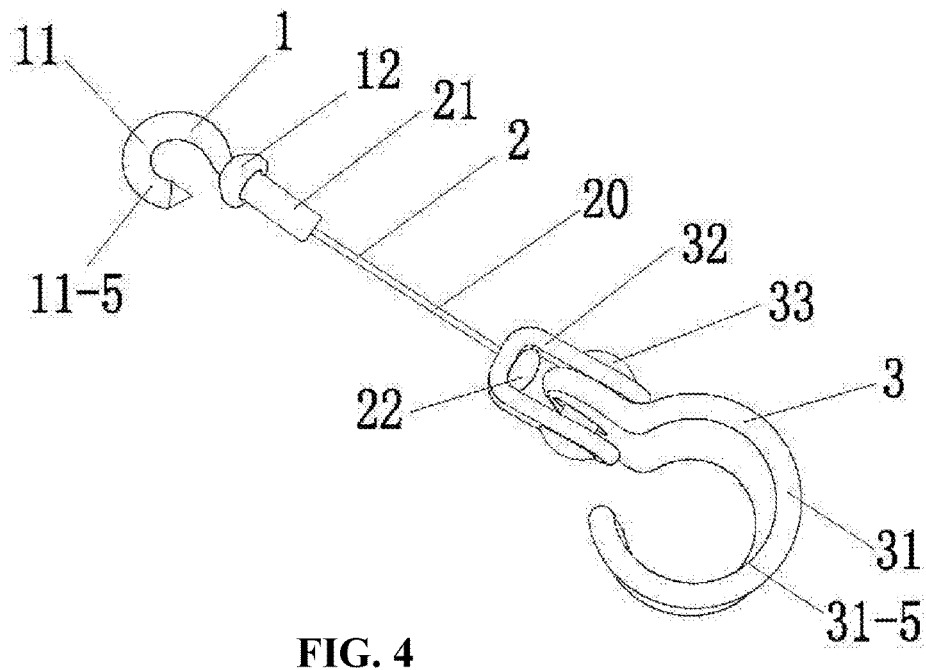
FIG. 4 is a structural schematic diagram of a connecting hook type lateral pharyngeal wall tractor in the present application.
Figures 1, 4:
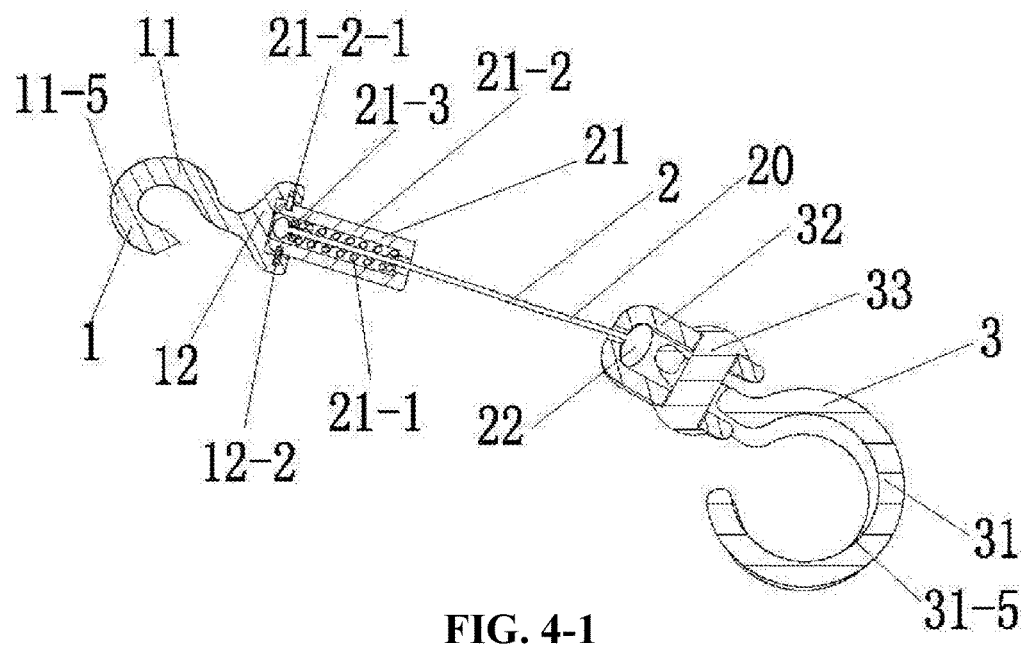
Figures 2, 4:
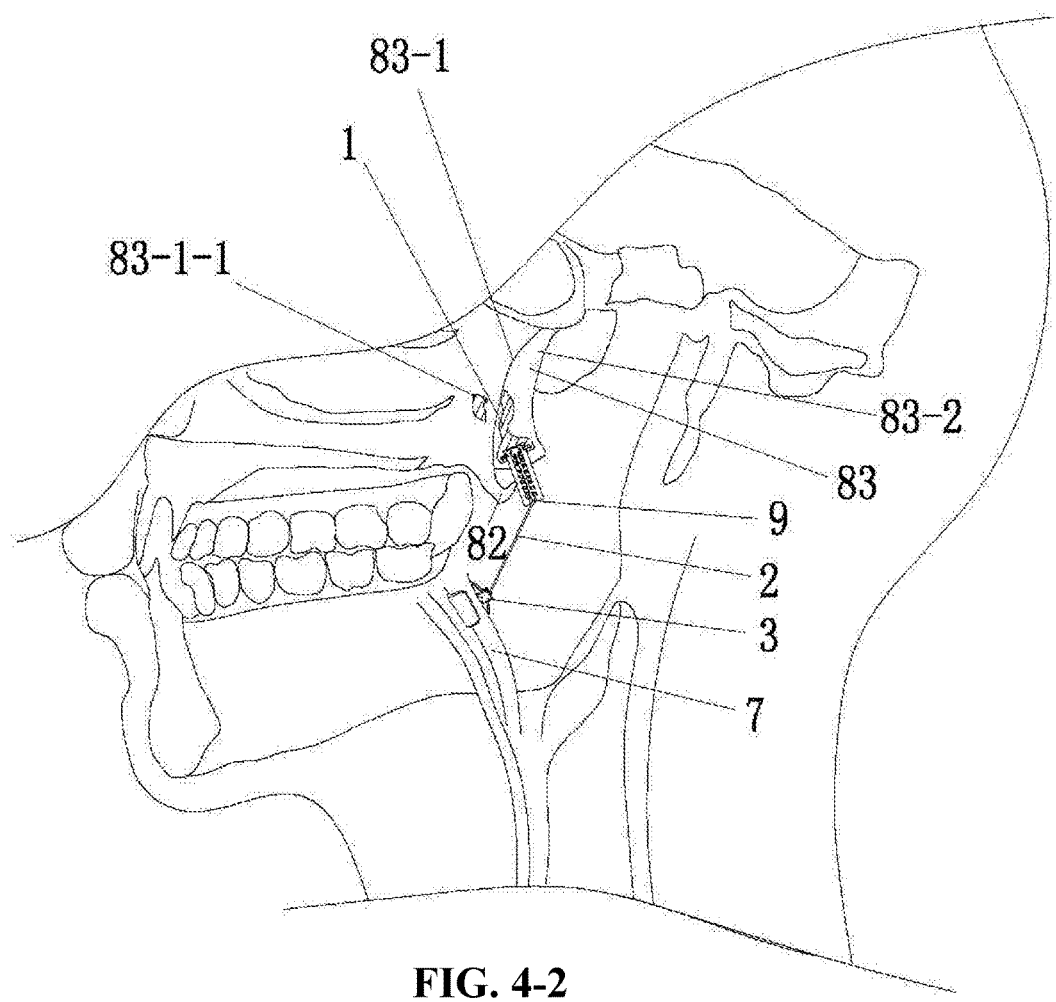

Referring to FIG. 4-2, in a clinical surgery:

Step 1: Under local anaethesia or general anaethesia, a mouth gag is put in, a vertical mucosal incision is made in the surface of a hamulus pterygoideus (82), a processus pterygoideus (83) is separated and exposed, and a through hole is made in a laminamedialis (83-1) or a laminalateralis (83-2) of the processus pterygoideus (83).

Step 2: An arc-shaped incision which is about 15 mm long is made along the upper end of a palatoglossal arch, an M. palatopharyngeus (7) is separated and exposed, or after routine UPPP, the M. palatopharyngeus (7) is exposed.

Step 3: A special tool is used to put in the lateral pharyngeal wall tractor (9) along the vertical mucosal incision of the surface of the hamulus pterygoideus (82), a lateral pharyngeal wall fixing mechanism (31) of a lateral pharyngeal wall fixer (3) is fixed on a submucous tissue of a lateral pharyngeal wall, such as the M. palatopharyngeus (7), by a method of claim 15, a traction mechanism (2) is connected to a connecting mechanism (12) of the bone fixer (1), and a connecting hook (11-5) of the bone fixer (1) is directly hung on the hamulus pterygoideus (82), or passes through the through hole (83-1-1) made in the laminamedialis (83-1) of the processus pterygoideus (83) to form connection.

Step 4: The tightness of the traction mechanism (2) is adjusted, the incision is sutured, and a surgery is performed on the opposite side in the same way.

Embodiment 5: A Lateral Pharyngeal Wall Tractor with a Connecting Ring Type Bone Fixer in the Present Application Referring to FIG. 5 and FIG. 5-2, the difference between the present embodiment and embodiment 2 is that in the present embodiment, a bone fixing mechanism (11) of the bone fixer (1) comprises a connecting ring (11-3). The connecting ring (11-3) is provided with a through hole (11-3-1), and can be put on a hamulus pterygoideus (82) to form connection.

Figure 5:
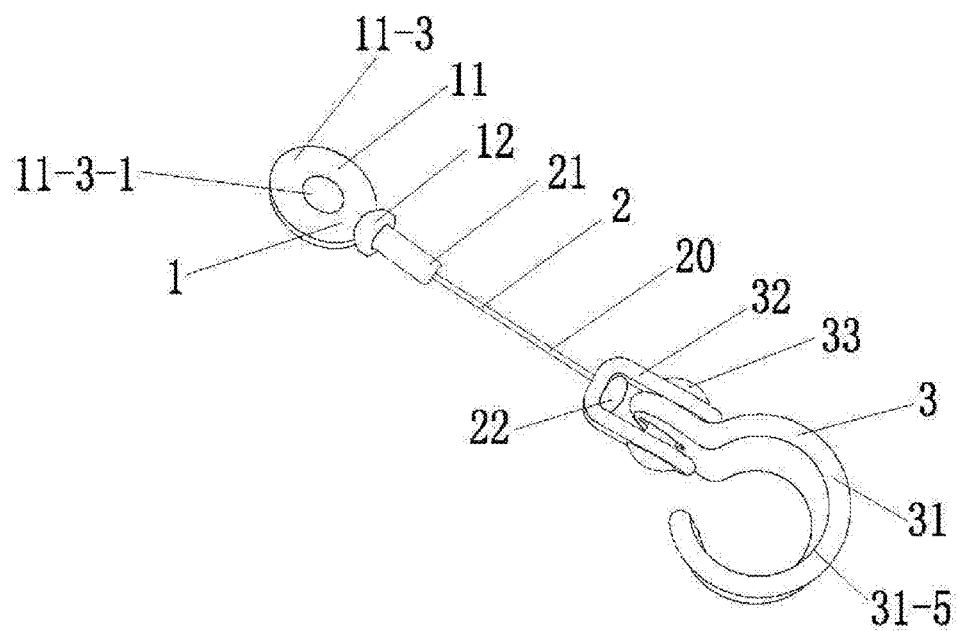
FIG. 5 is a structural schematic diagram of a connecting ring type lateral pharyngeal wall tractor in the present application.
Figures 1, 5:
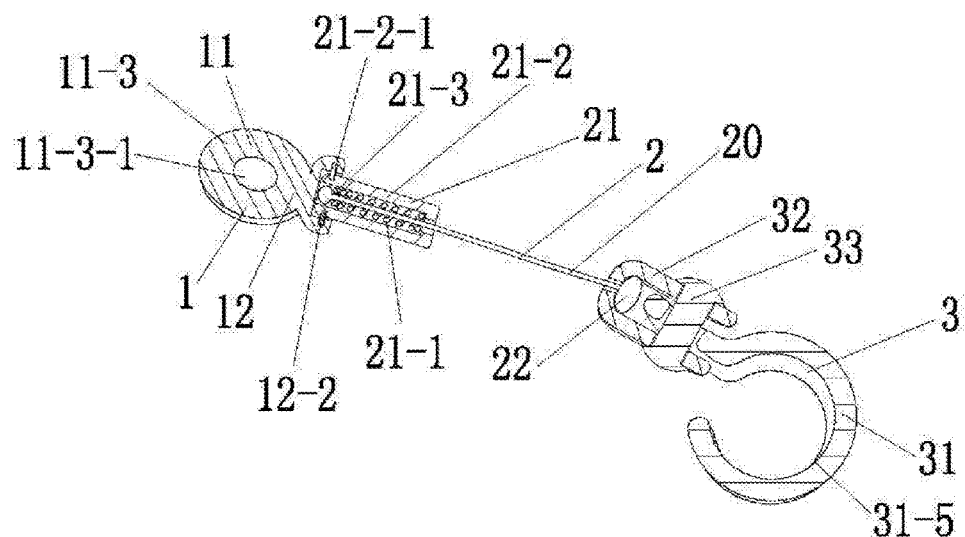
Figures 2, 5:
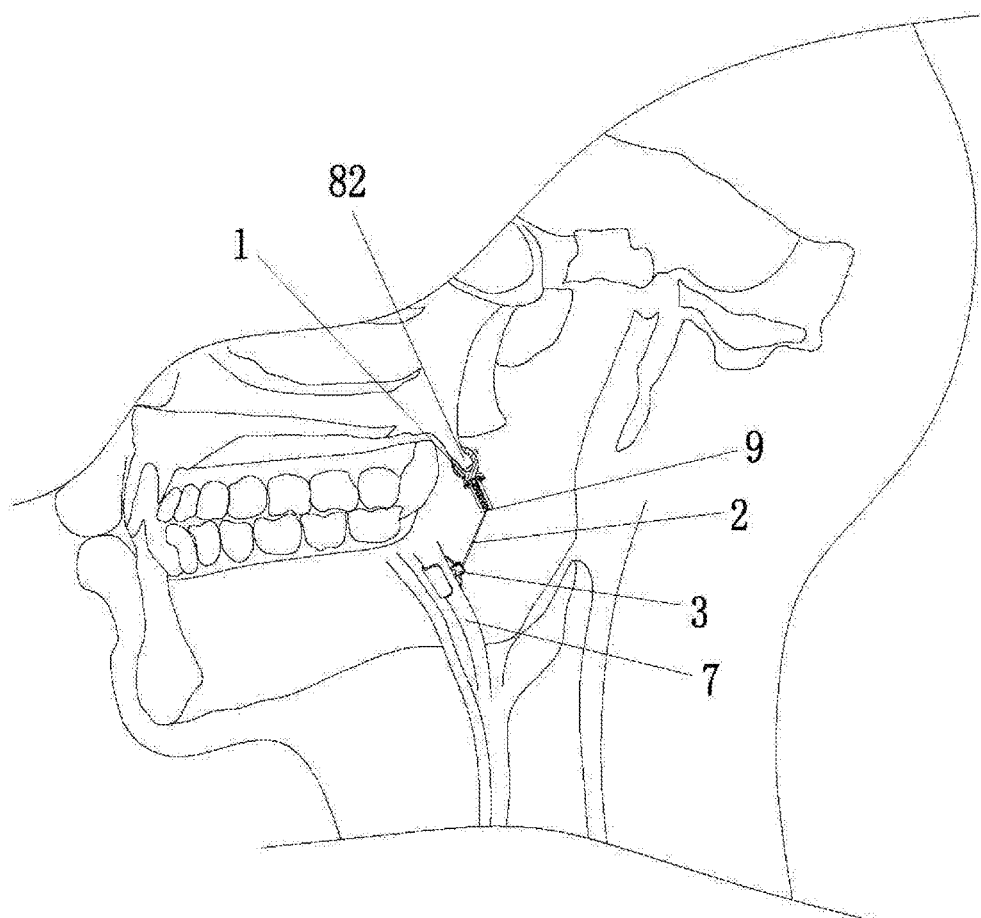

Referring to FIG. 5-2, in a clinical surgery:

Step 1: Under local anaethesia or general anaethesia, a mouth gag is put in, a vertical mucosal incision is made in the surface of a hamulus pterygoideus (82), and the hamulus pterygoideus (82) is separated and exposed.

Step 2: An arc-shaped incision which is about 15 mm long is made along the upper end of a palatoglossal arch, an M. palatopharyngeus (7) is separated and exposed, or after routine UPPP, the M. palatopharyngeus (7) is exposed.

Step 3: A special tool is used to put in the lateral pharyngeal wall tractor (9) along the vertical mucosal incision of the surface of the hamulus pterygoideus, a lateral pharyngeal wall fixing mechanism (31) of a lateral pharyngeal wall fixer (3) is fixed on a submucous tissue of a lateral pharyngeal wall, such as the M. palatopharyngeus (7), by a method of claim 15, a traction mechanism (2) is connected to a connecting mechanism (12) of the bone fixer (1), and the connecting ring (11-3) of the bone fixer (1) is put on the hamulus pterygoideus (82).

Step 4: The tightness of the traction mechanism (2) is adjusted, the incision is sutured, and a surgery is performed on the opposite side in the same way.

Embodiment 6: A Lateral Pharyngeal Wall Tractor with a Bone Claw Type Bone Fixer in the Present Application Referring to FIG. 6 and FIG. 6-2, the difference between the present embodiment and embodiment 2 is that in the present embodiment, a bone fixing mechanism (11) of the bone fixer (1) comprises a bone claw (11-2). The left arm and right arm of the bone claw (11-2) are provided with grip hooks (11-2-1). Clamping force which is produced between the left arm and right arm of the bone claw (11-2) and the grip hooks (11-2-1) enables the bone fixer (1) to clip a laminamedialis (83-1) or a laminalateralis (83-2) of a processus pterygoideus (83) to form fixation.

Figure 6:
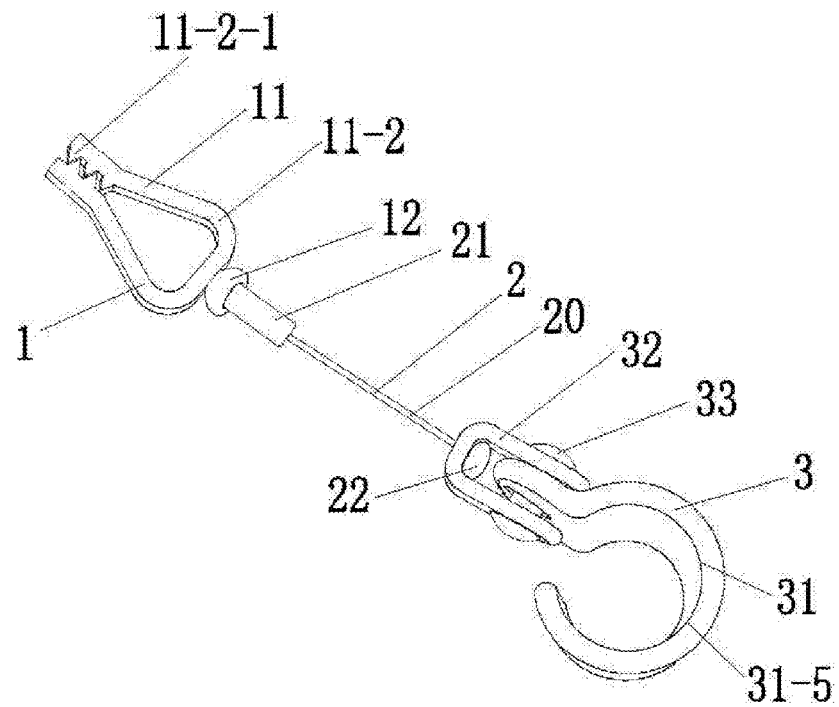
FIG. 6 is a structural schematic diagram of a bone claw type lateral pharyngeal wall tractor in the present application.
Figures 1, 6:
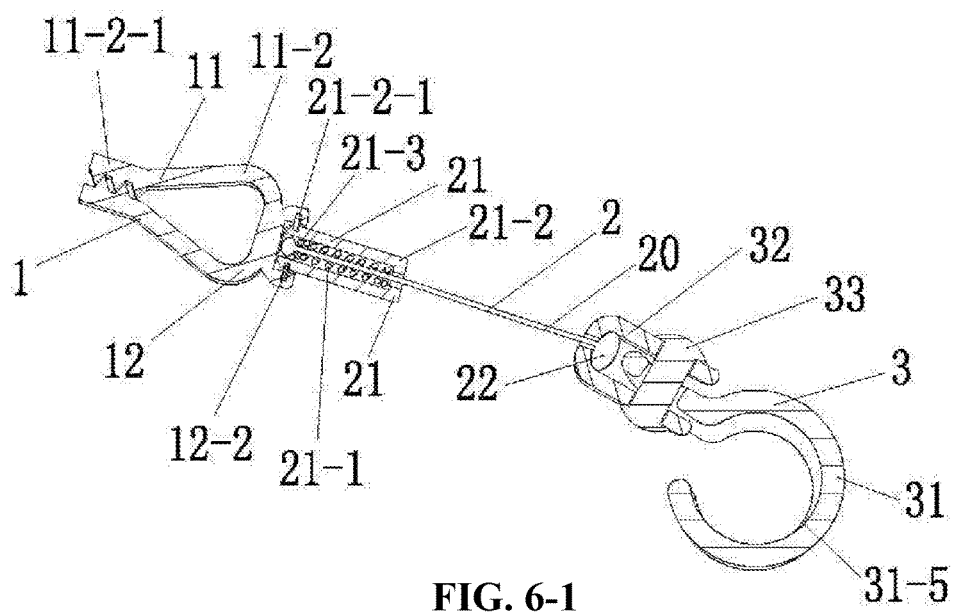
Figures 2, 6:
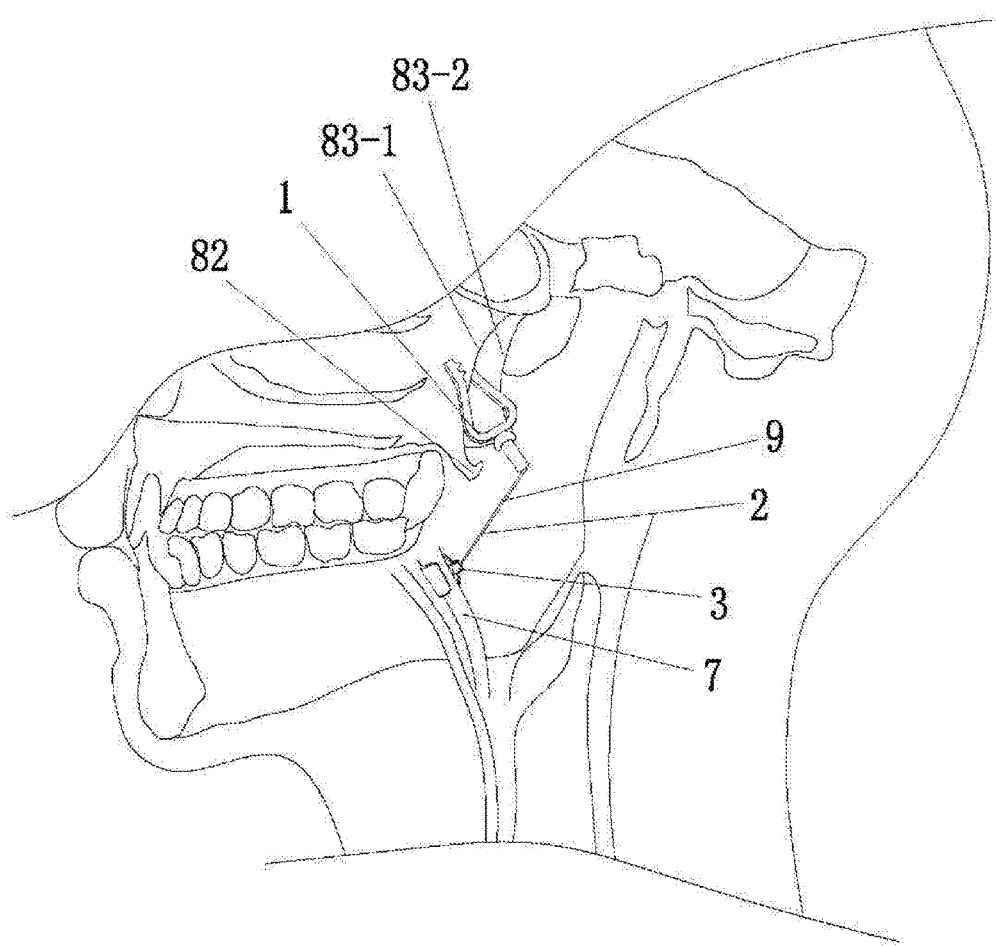

Referring to FIG. 6-2, in a clinical surgery:

Step 1: Under local anaethesia or general anaethesia, a mouth gag is put in, a vertical mucosal incision is made in the surface of a hamulus pterygoideus (82), the hamulus pterygoideus (82) or a processus pterygoideus (83) is separated and exposed, and grip hooks (11-2-1) of a bone claw (11-2) of a bone fixing mechanism (11) of a bone fixer (1) grip the hamulus pterygoideus (82) or the processus pterygoideus (83).

Step 2: An arc-shaped incision which is about 15 mm long is made along the upper end of a palatoglossal arch, an M. palatopharyngeus (7) is separated and exposed, or after routine UPPP, the M. palatopharyngeus (7) is exposed.

Step 3: A special tool is used to put in the lateral pharyngeal wall tractor (9) along the vertical mucosal incision of the surface of the hamulus pterygoideus, a lateral pharyngeal wall fixing mechanism (31) of a lateral pharyngeal wall fixer (3) is fixed on a submucous tissue of a lateral pharyngeal wall, such as the M. palatopharyngeus (7), by a method of claim 15, and after being connected to a connecting mechanism (12) of the bone fixer (1), a traction mechanism (2) is connected to the bone claw (11-2) of the bone fixing mechanism (11).

Step 4: The tightness of the traction mechanism (2) is adjusted, the incision is sutured, and a surgery is performed on the opposite side in the same way.

Figure 7:
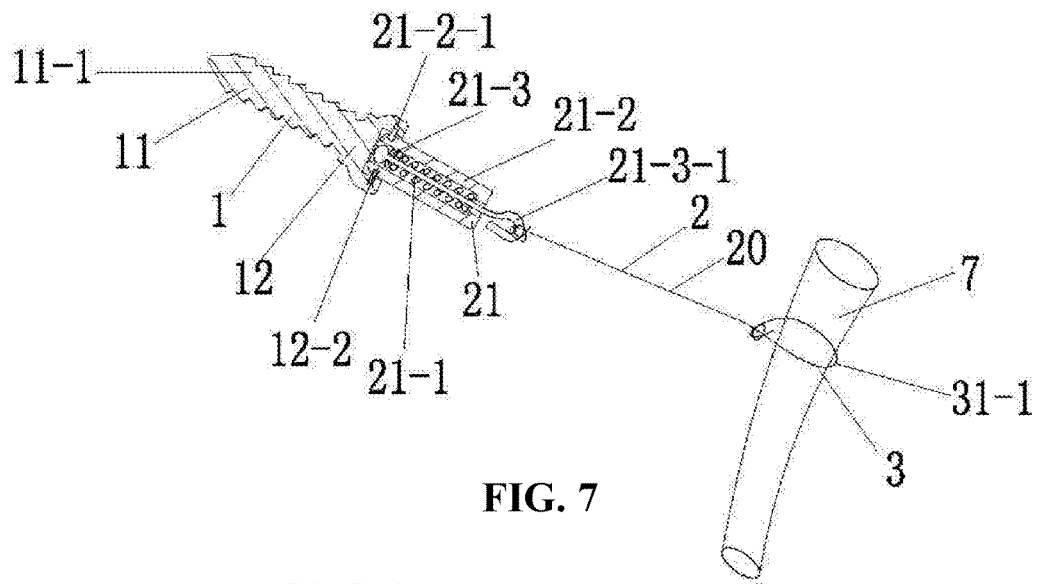
FIG. 7 is a structural schematic diagram of a binding thread type lateral pharyngeal wall tractor in the present application.

Embodiment 7: A Lateral Pharyngeal Wall Tractor with a Binding Thread Type Bone Fixer in the Present Application Referring to FIG. 7, the difference between the present embodiment and embodiment 2 is that a traction mechanism (2) comprises a thread (20) and an elasticity generator (21). The elasticity generator (21) comprises a spring mechanism (21-1), a shell (21-2) and a slider (21-3). The spring mechanism (21-1) adopts a non-dense coil spring. The shell (21-2) comprises a positioning groove (21-2-1). The slider (21-3) is arranged at the front end of the spring mechanism (21-1), and can slide in the shell (21-2). A connecting hook (21-3-1) is arranged on the slider (21-3). The bone fixer (1) comprises a bone fixing mechanism (11) and a connecting mechanism (12). The bone fixing mechanism (11) adopts a self-tapping threaded structure. A positioning plate (12-2) is arranged in the connecting cavity of the connecting mechanism (12). When the far end of the shell (21-2) of the elasticity generator (21) is inserted into the connecting cavity of the connecting mechanism (12), the positioning plate (12-2) is embedded in the positioning groove (21-2-1) of the shell (21-2), forming concave-convex engagement connection.

The thread (20) adopts an unabsorbable surgical suture. One end of the thread (20) is tied on a submucous tissue of a lateral pharyngeal wall, such as an M. palatopharyngeus (7), the other end is fixedly tied on the connecting hook (21-3-1) of the slider (21-3), and thereby connection is formed.

The present embodiment adopts a binding thread type lateral pharyngeal wall fixer (3), so the lateral pharyngeal wall tractor is very convenient when in clinical use; moreover, with the elasticity generator (21), the lateral pharyngeal wall tractor has a good force-cushioning effect, and therefore not only can prevent the collapse of a lateral pharyngeal wall, but also does not affect the function of deglutition.

Figure 8:
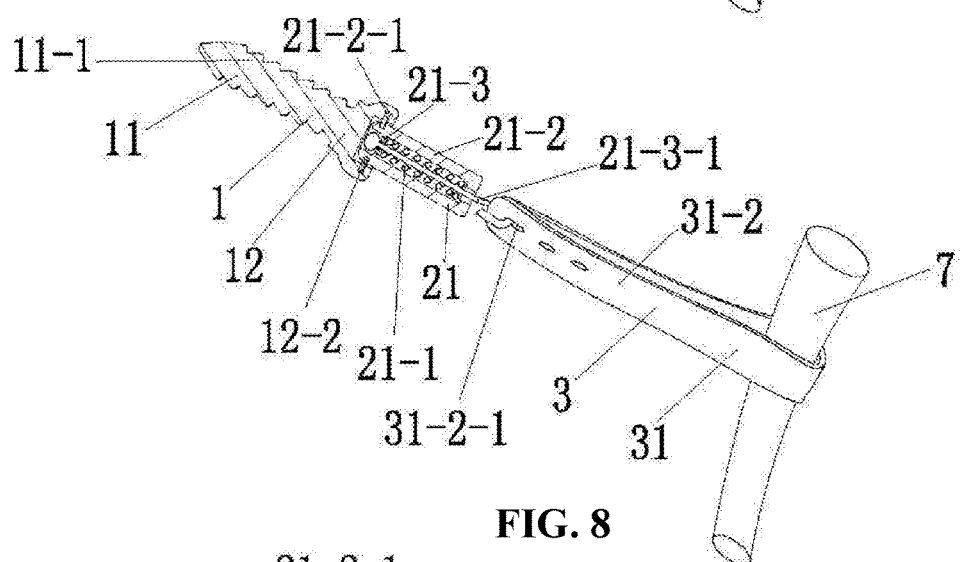
FIG. 8 is a structural schematic diagram of a binding strap type lateral pharyngeal wall tractor in the present application.

Embodiment 8: A Lateral Pharyngeal Wall Tractor with a Binding Strap Type Bone Fixer in the Present Application Referring to FIG. 8, the difference between the present embodiment and embodiment 7 is that in the present embodiment, a binding strap (31-2) is adopted to substitute for the binding thread (31-1) in embodiment 7. The binding strap (31-2) is provided with through holes (31-2-1). The through holes (31-2-1) enable the binding strap (31-2) to be hung on a connecting hook (21-3-1) of a slider (21-3) to form connection.

During clinical use, after rounding an M. palatopharyngeus (7), both ends of the binding strap (31-2) are hung on the connecting hook (21-3-1) of the slider (21-3), so that fixed connection is formed. The advantage of adopting the binding strap (31-2) is that compared with the binding thread (31-1), the binding strap (31-2) has a larger contact area, so that the M. palatopharyngeus (7) can be prevented from being cut.

Figure 9:
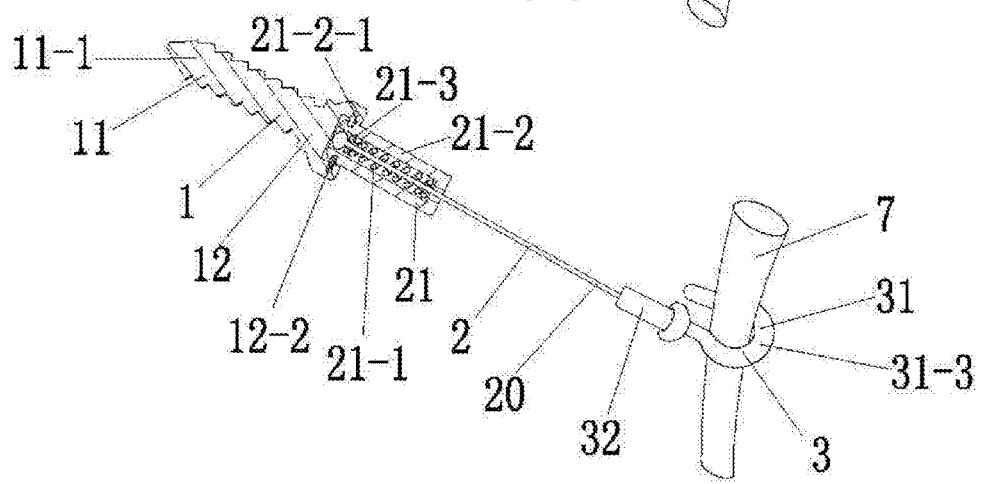
FIG. 9 is a structural schematic diagram of a fixing hook type lateral pharyngeal wall tractor in the present application.

Embodiment 9: A Lateral Pharyngeal Wall Tractor with a Fixing Hook Type Bone Fixer in the Present Application Referring to FIG. 9, compared with embodiment 7, the present embodiment has a difference that in the present embodiment, a lateral pharyngeal wall fixing mechanism (31) of a lateral pharyngeal wall fixer (3) comprises a fixing hook (31-3). The fixing hook (31-3) can hook an M. palatopharyngeus (7). The near end of the fixing hook (31-3) is provided with a connecting mechanism (32), and a thread (20) of a traction mechanism (2) is riveted on the connecting mechanism (32). The other end of the thread (20) is connected to the slider (21-3).

Embodiment 10: A Combined-Structure Curved Plate Type Lateral Pharyngeal Wall Tractor in the Present Application Referring to FIG. 10 to FIG. 10-2, compared with embodiment 2, the present embodiment has a difference that a lateral pharyngeal wall fixer (3) adopts a curved plate (31-5) with a combined structure. The curved fixing plate (31-5) with the combined structure comprises a reinforcing rib (31-5-1) and a film (31-5-2), and the film (31-5-2) is attached to the reinforcing rib (31-5-1). The reinforcing rib (31-5-1) or the film (31-5-2) can be elastically deformed under the action of external force, and can be restored or nearly restored to the original shape after the external force is removed. Titanium-nickel shape-memory alloy can be adopted to produce the reinforcing rib (31-5-1), so the reinforcing rib (31-5-1) has a shape-memory function, and therefore can automatically hold an M. palatopharyngeus (7). Medical silica gel or medical polyurethane is adopted to produce the film (31-5-2), or polypropylene or polytetrafluoroethylene can also be adopted to produce the film (31-5-2). Compared with a curved plate made of titanium alloy, the combined curved plate has better elasticity and flexibility, and therefore can better adapt to the deformation and motion of the M. palatopharyngeus (7) and has less affection on the function of deglutition.

Figure 11:
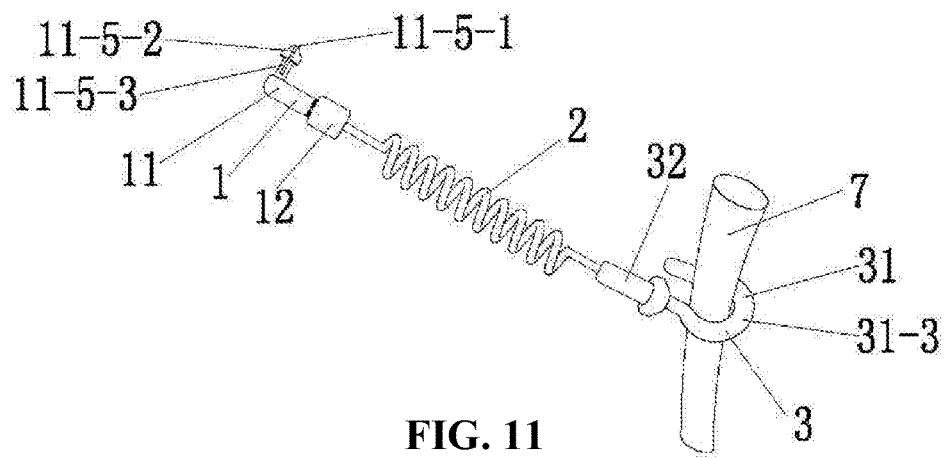
FIG. 11 is a structural schematic diagram of a lateral pharyngeal wall tractor comprising a spring mechanism in the present application.

Embodiment 11: A Lateral Pharyngeal Wall Tractor Comprising a Spring Mechanism in the Present Application Referring to FIG. 11, compared with embodiment 9, the present embodiment also adopts a lateral pharyngeal wall fixer (3) with a fixing hook type structure, but in the present embodiment, both a traction mechanism (2) and a bone fixer (1) are obviously different.

In the present embodiment, the bone fixer (1) comprises a connecting hook (11-5). The connecting hook (11-5) is provided with a slotted hole (11-5-1), a positioning convex step (11-5-2) and a positioning concave groove (11-5-3). After the connecting hook (11-5) passes through a through hole (83-1-1) made in a laminamedialis (83-1) of a processus pterygoideus (83) or a through hole (83-2-1) made in a laminalateralis (83-2) of the processus pterygoideus (83), the positioning convex step (11-5-2) can fix the connecting hook (11-5) on the laminamedialis (83-1) or laminalateralis (83-2) of the processus pterygoideus (83) and prevent slipping.

The middle of the traction mechanism (2) is provided with the spring mechanism (21-1). The spring mechanism (21-1) is a coil spring.

The spring mechanism (21-1) can have a good force-cushioning effect, and therefore not only can prevent the collapse of a lateral pharyngeal wall, but also does not affect the function of deglutition.

Figure 12:
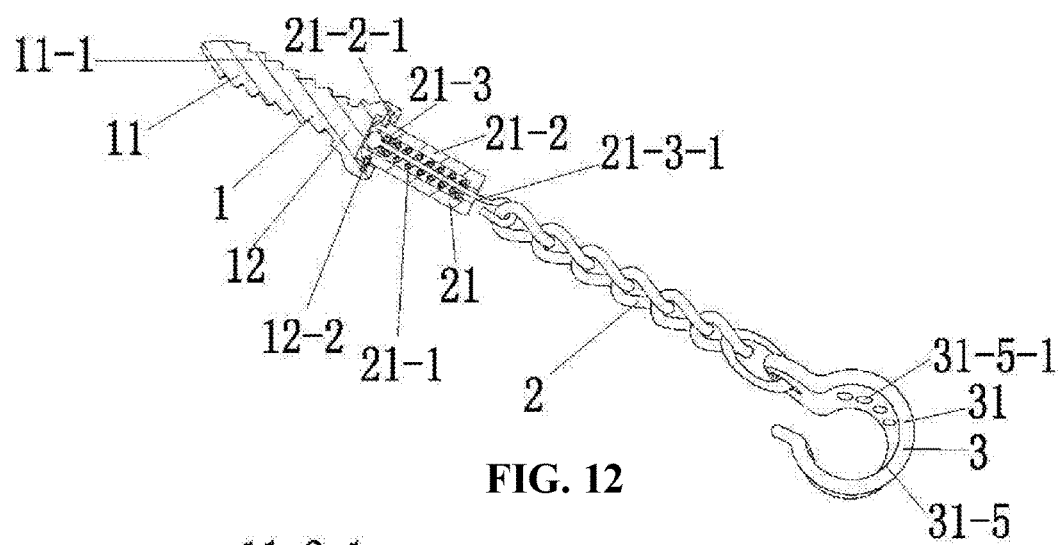
FIG. 12 is a structural schematic diagram of a lateral pharyngeal wall tractor comprising a traction mechanism with a linear structure in the present application.

Embodiment 12: A Lateral Pharyngeal Wall Tractor Comprising a Traction Mechanism with a Linear Structure in the Present Application Referring to FIG. 12, the difference between the present embodiment and embodiment 7 is that in the present embodiment, a lateral pharyngeal wall fixer (3) comprises a U-shaped curved plate (31-5). The U-shaped curved plate (31-5) is provided with through holes (31-5-1). A lateral pharyngeal wall tissue can conveniently grow to pass through the through holes (31-5-1), so that the U-shaped curved plate (31-5) and the lateral pharyngeal wall tissue can be conveniently fixed together.

The traction mechanism (2) adopts the chain-shaped linear structure, one end of the traction mechanism (2) with the chain-shaped structure is hung on a connecting hook (21-3-1) of a slider (21-3), and the other end is connected to the through hole of a connecting mechanism (32) of a lateral pharyngeal wall fixer (3). The present application is very convenient when in clinical use.

Figure 13:
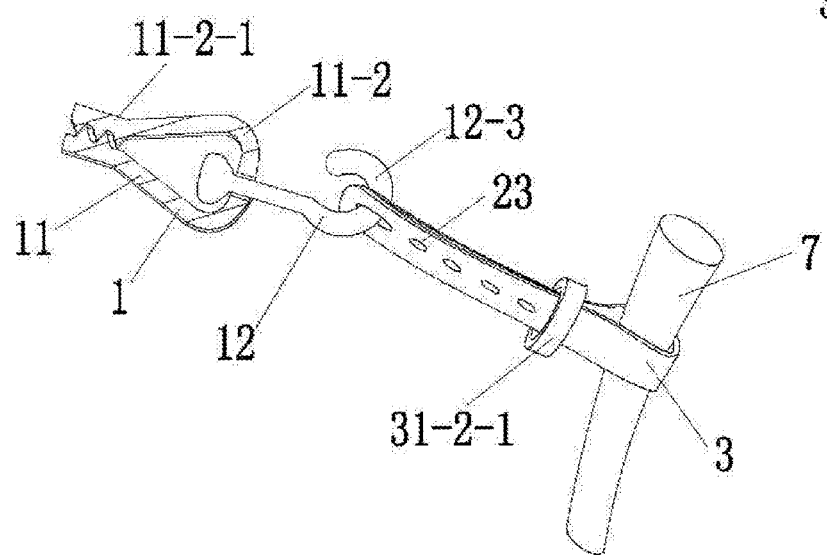
FIG. 13 is a structural schematic diagram of a lateral pharyngeal wall tractor comprising an elastic strap-shaped lateral pharyngeal wall fixer in the present application.

Embodiment 13: A Lateral Pharyngeal Wall Tractor Comprising an Elastic Strap-Shaped Lateral Pharyngeal Wall Fixer in the Present Application Referring to FIG. 13, in the present embodiment, a bone fixer (1) comprises a bone claw (11-2), and the left arm and right arm of the bone claw (11-2) are provided with grip hooks (11-2-1). Clamping force which is produced between the left arm and right arm of the bone claw (11-2) and the grip hooks (11-2-1) enables the bone fixer (1) to clip a laminamedialis (83-1) or a laminalateralis (83-2) of a processus pterygoideus (83) to form fixation.

The tail of the bone claw (11-2) of the bone fixer (1) is provided with a connecting mechanism (12), and the connecting mechanism (12) comprises a connecting hook (12-3). A traction mechanism (2) and the lateral pharyngeal wall fixer (3) are of a flat structure which is made of medical silica gel as a whole, and are provided with through holes (23). The through holes (23) can be hung on the connecting hook (12-3) of the bone fixer (1) to form connection. The lateral pharyngeal wall fixer (3) comprises a positioning ring (31-2-1). The positioning ring (31-2-1) is an annular ring made of medical silica gel. During use, one end of the traction mechanism (2) and the lateral pharyngeal wall fixer (3) produced as a whole is hung on the connecting hook (12-3) through the through holes (23), and after rounding an M. palatopharyngeus (7) and passing through the positioning ring (31-2-1), the other end is hung on the connecting hook (12-3), and thereby connection is formed.

Since the medical silica gel itself has excellent biocompatibility and good elasticity, the medical silica gel has a good force-cushioning effect, and therefore not only can prevent the collapse of a lateral pharyngeal wall, but also does not affect the function of deglutition.

Figure 14:
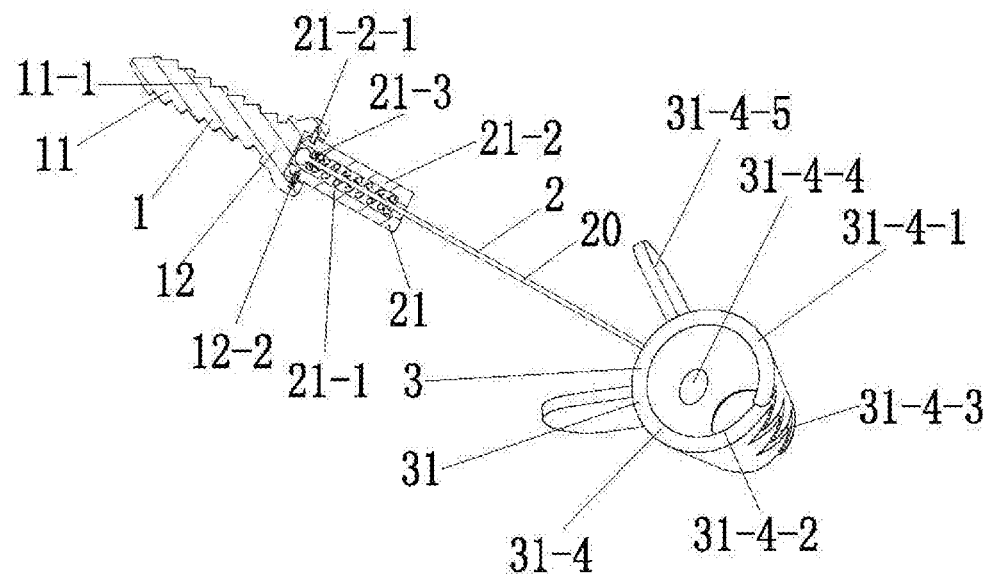
FIG. 14 is a structural schematic diagram of an elastic material-made tissue clip type lateral pharyngeal wall tractor in the present application.
Figures 1, 14:
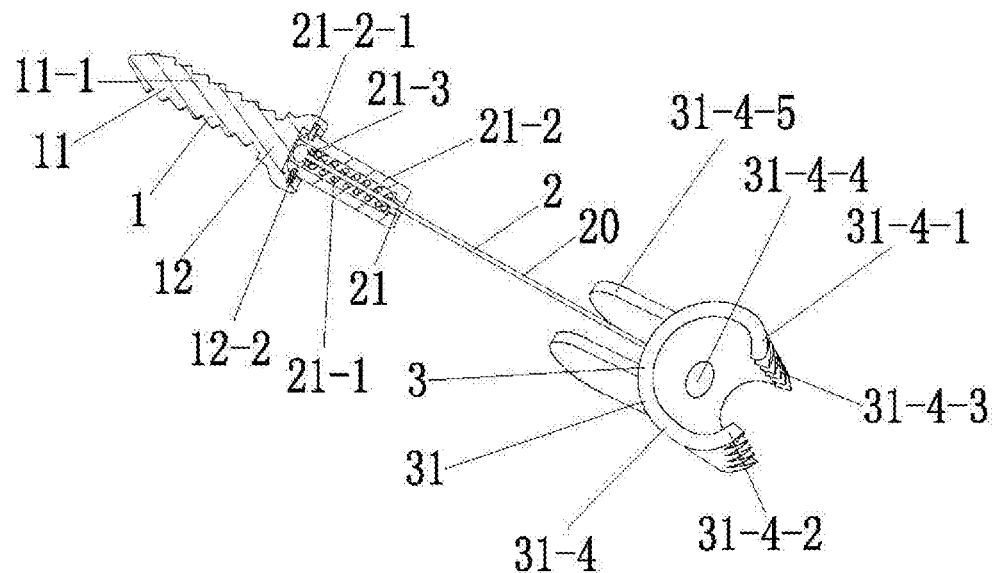

Embodiment 14: An Elastic Material-Made Tissue Clip Type Lateral Pharyngeal Wall Tractor in the Present Application Referring to FIG. 14 and FIG. 14-1, in the present embodiment, a lateral pharyngeal wall fixer (3) comprises a tissue clip (31-4), and the tissue clip (31-4) is made of a medical elastic metal material, and is of a C-shaped clip structure. The tissue clip (31-4) comprises a left arm (31-4-1), a right arm (31-4-2), occludable teeth (31-4-3), a through hole (31-4-4) and handles (31-4-5). The left arm (31-4-1) and the right arm (31-4-2) can be opened by pressing the handles (31-4-5), so that a lateral pharyngeal wall tissue, such as an M. palatopharyngeus (7), can be conveniently clipped. The through hole (31-4-4) can be connected to a thread (20) of a traction mechanism (2), playing the role of a connecting mechanism (32). When the handles (31-4-5) are released, under the action of resilience, the left arm (31-4-1) and the right arm (31-4-2) automatically close, the occludable teeth (31-4-3) automatically occlude, and thereby a closed structure is formed to prevent the tissue clipped in the tissue clip (31-4) from slipping off.

Figure 15:
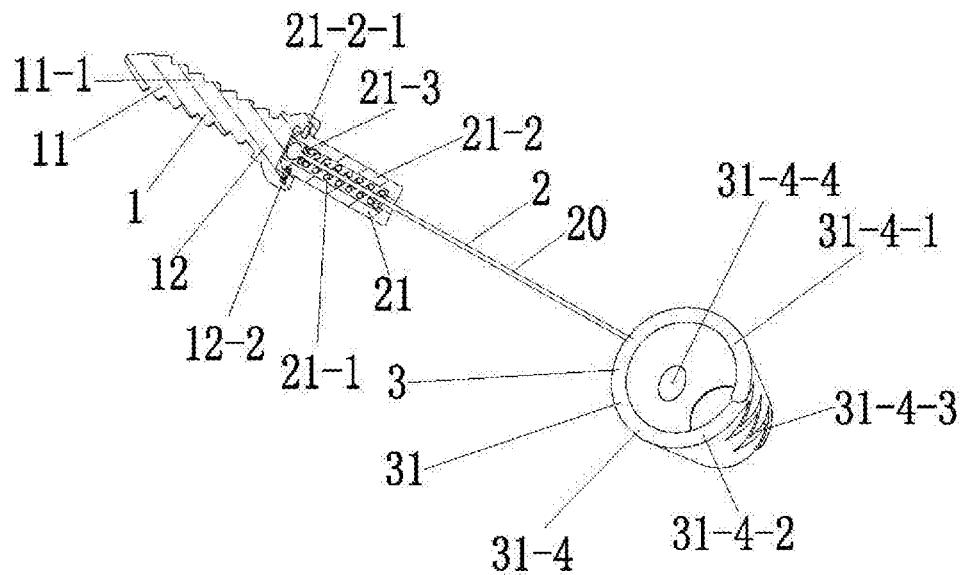
FIG. 15 is a structural schematic diagram of a shape-memory alloy material-made tissue clip type lateral pharyngeal wall tractor in the present application.
Figures 1, 15:
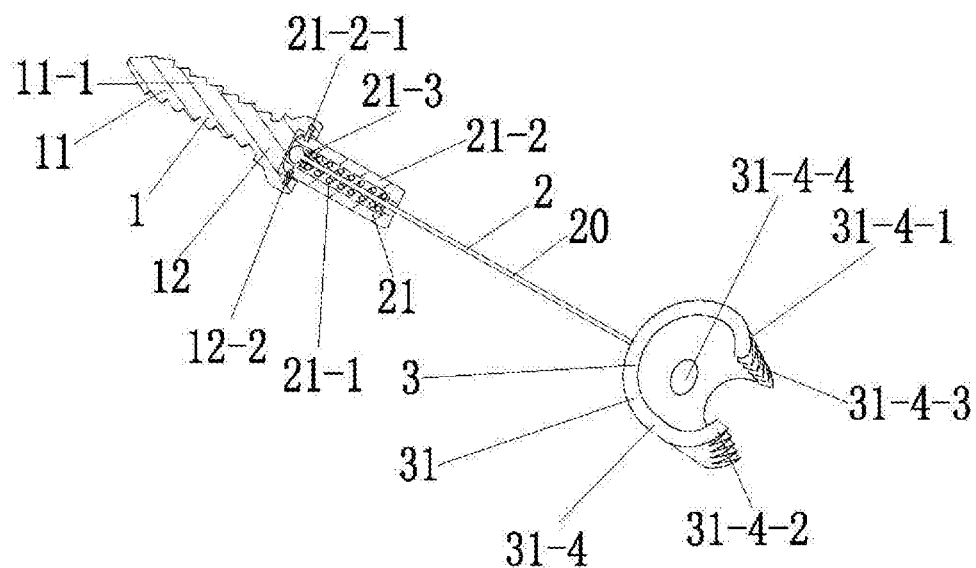

Embodiment 15: A Shape-Memory Alloy Material-Made Tissue Clip Type Lateral Pharyngeal Wall Tractor in the Present Application Referring to FIG. 15 and FIG. 15-1, the difference between the present embodiment and embodiment 14 is that in the present embodiment, titanium-nickel shape-memory alloy is adopted to produce a tissue clip (31-4), and thus, handles do not need to be arranged. Under low temperature, such as 15° C., the tissue clip (31-4) is opened, referring to FIG. 15-1. After the tissue clip (31-4) is implanted into the human body, under the effect of body temperature, the titanium-nickel shape-memory alloy exceeds its restoring temperature, the tissue clip (31-4) is automatically restored to the originally set shape, the left arm (31-4-1) and right arm (31-4-2) of the tissue clip (31-4) automatically close, the occludable teeth (31-4-3) automatically occlude, and thereby a tissue clipped in the tissue clip (31-4) can be prevented from slipping off.

Of course, plastic materials, such as a pure titanium plate, can also be adopted to produce the tissue clip (31-4). During use, external force is first used to open the left arm (31-4-1) and right arm (31-4-2) of the tissue clip (31-4), and after an M. palatopharyngeus (7) is put in, external force is used to close the tissue clip (31-4).

Figure 16:
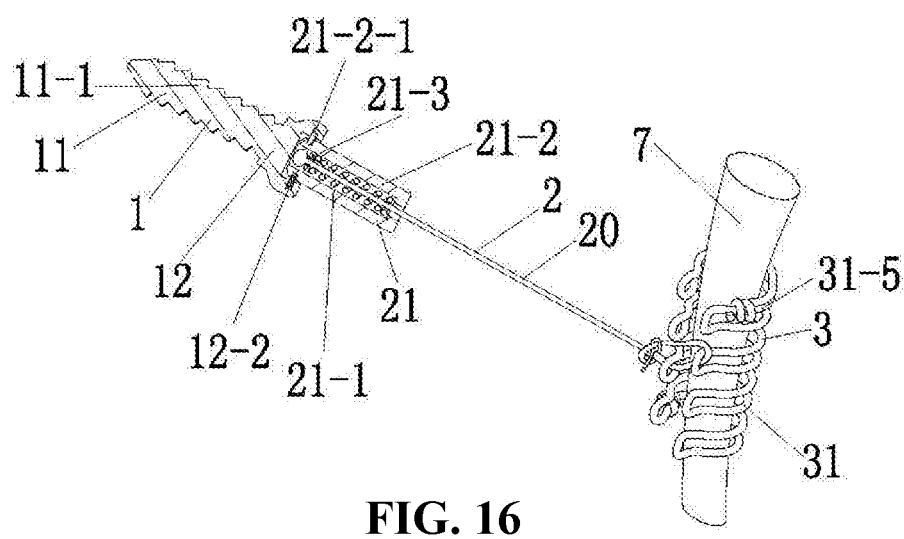
FIG. 16 is a structural schematic diagram of a single wire-wound helical C-shaped curved plate type lateral pharyngeal wall tractor in the present application.

Embodiment 16: A Single Wire-Wound Helical C-Shaped Curved Plate Type Lateral Pharyngeal Wall Tractor in the Present Application Referring to FIG. 16, the difference between the present embodiment and embodiment 10 is that in the present embodiment, a curved fixing plate (31-5) adopts a single wire-wound helical C-shaped curved plate. Specially, a titanium-nickel shape-memory alloy wire can be adopted to produce the curved fixing plate (31-5). Other medical elastic materials can also be adopted for production.

Since the curved plate (31-5) adopts the single wire-wound helical structure, a thread (20) of a traction mechanism (2) can be easily tied in the helical through hole of the C-shaped curved plate (31-5) to form connection. Compared with embodiment 10, the present embodiment is more convenient to install when in use.

It should be noted that the structures disclosed and described herein can be substituted by other structures with the same effect, and moreover, the embodiments introduced in the present application are not the only structures implementing the present application. Although the preferred embodiments of the present application have been introduced and described herein, those skilled in the art may all clearly know that these embodiments are merely described as examples, those skilled in the art can make innumerable variations, improvements and substitutes without departing from the present application, and therefore, the protection scope of the present application should be defined according to the spirit and scope of the claims attached to the present application.

What is claimed is:

1. A lateral pharyngeal wall tractor, comprising:
 a bone fixer, a traction mechanism and a lateral pharyngeal wall fixer;
 wherein the bone fixer is provided with a bone fixing mechanism configured to be fixed on one of a processus alveolaris, a hamulus pterygoideus and a processus pterygoideus and a connecting mechanism configured to be connected to the traction mechanism; and the bone fixing mechanism and the connecting mechanism are connected together;
 the traction mechanism is one of a thread, a linear mechanism and a flat mechanism that is made of a material capable of being implanted in a human body for a long time;
 the lateral pharyngeal wall fixer is provided with a lateral pharyngeal wall fixing mechanism configured to be fixed on a lateral pharyngeal wall and a connecting mechanism configured to be connected to the traction mechanism, and the lateral pharyngeal wall fixing mechanism and the connecting mechanism are connected together; and
 the bone fixing mechanism of the bone fixer is configured to be fixed on the one of the processus alveolaris, hamulus pterygoideus and processus pterygoideus of a third molar of maxilla;
 the lateral pharyngeal wall fixing mechanism of the lateral pharyngeal wall fixer is configured to be fixed on an M. palatopharyngeus or other submucous tissues of the lateral pharyngeal wall;

one end of the traction mechanism is fixed on the connecting mechanism of the lateral pharyngeal wall fixer, and the other end is fixed on the connecting mechanism of the bone fixer; and the bone fixer and the lateral pharyngeal wall fixer are connected together through the traction mechanism.

2. The lateral pharyngeal wall tractor according to claim 1, characterized in that the lateral pharyngeal wall fixing mechanism of the lateral pharyngeal wall fixer is a binding thread, a binding strap, a fixing hook, a tissue clip or a curved fixing plate configured to be tied or configured to be fixed on the submucous tissue of the lateral pharyngeal wall.

3. The lateral pharyngeal wall tractor according to claim 2, characterized in that the curved fixing plate is a curved fixing plate with a combined structure, the curved fixing plate with the combined structure comprises a reinforcing rib and a film, and the film is attached to the reinforcing rib.

4. The lateral pharyngeal wall tractor according to claim 3, characterized in that the reinforcing rib or the film can be elastically deformed under an action of an external force, and can be restored or nearly restored to an original shape after the external force is removed.

5. The lateral pharyngeal wall tractor according to claim 2, characterized in that the curved fixing plate is a C-shaped or U-shaped curved fixing plate.

6. The lateral pharyngeal wall tractor according to claim 2, characterized in that the curved fixing plate adopts a helical C-shaped curved plate which is made of a single wire by winding.

7. The lateral pharyngeal wall tractor according to claim 1, wherein the traction mechanism comprises an elasticity generator which can generate elastic traction force.

8. The lateral pharyngeal wall tractor according to claim 7, characterized in that the elasticity generator comprises a spring mechanism.

9. The lateral pharyngeal wall tractor according to claim 7, characterized in that the elasticity generator comprises the spring mechanism, a shell and a slider capable of being connected to the thread; and the spring mechanism and the slider are movably installed in the shell.

10. The lateral pharyngeal wall tractor according to claim 7, characterized in that the traction mechanism comprises at least one elasticity generator; the elasticity generators are arranged at both ends of the traction mechanism, or the elasticity generator is arranged in the middle of the traction mechanism.

11. The lateral pharyngeal wall tractor according to claim 1, wherein the bone fixing mechanism of the bone fixer comprises a bone nail.

12. The lateral pharyngeal wall tractor according to claim 11, wherein the bone nail is a threaded bone nail which is made of a material capable of being implanted in a human body for a long time.

13. The lateral pharyngeal wall tractor according to claim 1, wherein the traction mechanism comprises a thread which is made of a material configured to be implanted in a human body for a long time.

14. The lateral pharyngeal wall tractor according to claim 13, wherein the thread is a thread with elasticity.

15. The lateral pharyngeal wall tractor according to claim 1, wherein the bone fixing mechanism of the bone fixer comprises a bone claw configured to be fixed on the hamulus pterygoideus or the processus pterygoideus, and the bone claw is provided with grip hooks.

16. The lateral pharyngeal wall tractor according to claim 1, wherein the bone fixing mechanism of the bone fixer comprises a connecting ring configured to be positioned on the hamulus pterygoideus, and the connecting ring is provided with a through hole through which the hamulus pterygoideus can pass.

17. The lateral pharyngeal wall tractor according to claim 1, wherein the bone fixing mechanism of the bone fixer comprises a support configured to be embedded in the processus pterygoideus, the support is provided with supporting legs, and the supporting legs are respectively configured to be fixed on a laminamedialis and a laminalateralis of the processus pterygoideus.

18. The lateral pharyngeal wall tractor according to claim 1, wherein the bone fixing mechanism of the bone fixer comprises a connecting hook configured to be hung on the hamulus pterygoideus or the processus pterygoideus.

19. The lateral pharyngeal wall tractor according to claim 1, characterized in that an elastic traction force of the traction mechanism is greater than a collapse force of the lateral pharyngeal wall which is produced by negative pressure during inspiration, but is less than a contraction force which is produced by muscle of the lateral pharyngeal wall during deglutition.

* * * * *